US012594303B2

(12) United States Patent
Kim et al.

(10) Patent No.: US 12,594,303 B2
(45) Date of Patent: Apr. 7, 2026

(54) COMPOSITION COMPRISING EXOSOMES DERIVED FROM INDUCED PLURIPOTENT STEM CELL-DERIVED MESENCHYMAL STEM CELL PROGENITOR FOR PREVENTION OR TREATMENT OF NON-ALCOHOLIC STEATOHEPATITIS

(71) Applicant: BREXOGEN INC., Seoul (KR)

(72) Inventors: Sue Kim, Seoul (KR); Seulki Lee, Gyeonggi-do (KR); Jimin Kim, Seoul (KR)

(73) Assignee: BREXOGEN INC., Seoul (KR)

( * ) Notice: Subject to any disclaimer, the term of this patent is extended or adjusted under 35 U.S.C. 154(b) by 645 days.

(21) Appl. No.: 17/621,743

(22) PCT Filed: Aug. 12, 2020

(86) PCT No.: PCT/KR2020/010640
§ 371 (c)(1),
(2) Date: Dec. 22, 2021

(87) PCT Pub. No.: WO2021/033990
PCT Pub. Date: Feb. 25, 2021

(65) Prior Publication Data
US 2022/0233601 A1     Jul. 28, 2022

(30) Foreign Application Priority Data

Aug. 22, 2019     (KR) ........................ 10-2019-0103186
Aug. 4, 2020     (KR) ........................ 10-2020-0097398

(51) Int. Cl.
| | |
|---|---|
| A61K 35/28 | (2015.01) |
| A61P 1/16 | (2006.01) |
| C12N 5/0775 | (2010.01) |

(52) U.S. Cl.
CPC ................. *A61K 35/28* (2013.01); *A61P 1/16* (2018.01); *C12N 5/0663* (2013.01); *C12N 2501/335* (2013.01); *C12N 2501/999* (2013.01); *C12N 2506/45* (2013.01)

(58) Field of Classification Search
CPC .................. A61K 35/28; A61K 35/545; C12N 2501/335; C12N 2506/45; C12N 2500/36; C12N 5/0668
See application file for complete search history.

(56) References Cited

U.S. PATENT DOCUMENTS 8,389,472 B2     3/2013     Baron et al.

FOREIGN PATENT DOCUMENTS

| | | | |
|---|---|---|---|
| KR | 10-2019-0015106 A | 2/2019 | |
| WO | WO-2019031729 A2 * | 2/2019 | ............ A23L 33/10 |

OTHER PUBLICATIONS

Zomer et. al. (Mesenchymal and induced pluripotent stem cells: general insights and clinical perspectives, Stem Cells and Cloning: Advances and Applications 2015:8 125-134). (Year: 2015).*

Ding et al. (Exendin-4, a Glucagon-Like Protein-1 (GLP-1) Receptor Agonist, Reverses Hepatic Steatosis in ob/ob Mice, Hepatology, Jan. 2006; 43(1): 173-181). (Year: 2006).*

WO-2019031729-A2 translated doc, 19 pages. (Year: 2019).*

Johnsen et. al. "A comprehensive overview of exosomes as drug delivery vehicles—Endogenous nanocarriers for targeted cancer therapy", Biochimica et Biophysica Acta 1845 (2014) 75-87; doi:10.1016/j.bbcan.2014.04.005. (Year: 2014).*

Sivasubramaniyan (Expression of stage-specific embryonic antigen-4 (SSEA-4) defines spontaneous loss of epithelial phenotype in huma solid tumor cells, Glycobiology, 2015, vol. 25, No. 8, 902-917). (Year: 2015).*

Extended European Search Report from corresponding European Patent Application No. 20855301.6, dated Sep. 2, 2022.

Nong, K., et al.; "Hemopatoprotective effect of exosomes from human-induced pluripotent stem cell-derived mesenchymal stromal cells against heptic ischemia-reperfusion injury in rats", Cytotherapy, 2016, 18; 1548-1559.

Fiore, E. J., et al.; "Taking advantage of the potential of mesenchymal stromal cells in liver regeneration: Cells and extracellular vesicles as therapeutic strategies", World J Gastroenterol, 2018, 24(23); 2427-2440.

Kim, S., et al.; "Exosomes Secreted from Induced Pluripotent Stem Cell-Derived Mesenchymal Stem Cells Accelerate Skin Cell Proliferation", International Journal of Molecular Sciences, 2018, 19, 2119, pp. 1-16.

Ohara, M., et al.; "Extracellular Vesicles from Amnion-Derived Mesnchymal Stem Cells Ameliorate Hepatic Inflammation and Fibrosis in Rats", Stem Cells International, p. 1-14.

Journal of Hepatology 2017 vol. 66, p. 1.

Fiore, E. J., et al.; "Taking advantage of the potential of mesenchymal stromal cells in liver regeneration: Cells and extracellular vesicles as therapeutic strategies", World J Gastroenterol Jun. 21, 2018; 24(23): 2427-2440.

Kim, S., et al.; "Exosomes Secreted from Induced Pluripotent Stem Cell-Derived Mesenchymal Stem Cells Accelerate Skin Cell Proliferation", Int. J. Mol. Sci. 2018, 19, 3119, pp. 1-16.

Liu, J., et al.; "Exendin-4 Pretreated Adipose Derived Stem Cells Are Resistant to Oxidative Stress and Improve Cardiac Performance via Enhanced Adhesion in the Infarcted Heart", PLOS One, Jun. 2014, vol. 9, Issue 6, pp. 1-12.

(Continued)

*Primary Examiner* — Anand U Desai
*Assistant Examiner* — Jacob A Boeckelman
(74) *Attorney, Agent, or Firm* — Harness, Dickey & Pierce, P.L.C.

(57) ABSTRACT

The present disclosure relates to a pharmaceutical composition for prevention or treatment of non-alcoholic steatohepatitis, the composition comprising, as an active ingredient, exosomes isolated from induced pluripotent stem cell-derived mesenchymal stem cells which have been or have not been treated with a pretreatment material. The exosomes of the present disclosure exhibit a more improved effect of preventing or treating non-alcoholic steatohepatitis, compared to those isolated from conventional mesenchymal stem cells and as such, can be advantageously used for relevant research and development, and productization.

2 Claims, 32 Drawing Sheets

Specification includes a Sequence Listing.

(56) References Cited

OTHER PUBLICATIONS

Nong, K., et al.; "Hepatoprotective effect of exosomes from human-induced pluripotent stem cell-derived mesenchymal stromal cells against hepatic ischemia-reperfusion injury in rats", Cytotherapy, 2016; 18: 1548-1559.

Du, Y., et al.; "Exosomes from Human-Induced Pluripotent Stem Cell-Derived Mesenchymal Stromal Cells (hiPSC-MSCs) Protect Liver against Hepatic Ischemia/ Reperfusion Injury via Activating Sphingosine Kinase and Sphingosine-1-Phosphate Signaling Pathway", Cell Physiol Biochem 2017;43:611-625.

International Search Report from corresponding PCT Application No. PCT/KR2020/010640, issued on Dec. 2, 2020.

* cited by examiner

BxC-e

BxC-V37e

BxC-G63e

TAA-V37e

TAA-PBS

Normal

TAA-G63e

TAA-PBS

Normal

COMPOSITION COMPRISING EXOSOMES DERIVED FROM INDUCED PLURIPOTENT STEM CELL-DERIVED MESENCHYMAL STEM CELL PROGENITOR FOR PREVENTION OR TREATMENT OF NON-ALCOHOLIC STEATOHEPATITIS

CROSS-REFERENCE TO RELATED APPLICATIONS

This application is a national phase application of PCT Application No. PCT/KR2020/010640, filed on 12 Aug. 2020, which claims the benefit and priority to Korean Patent Application Nos. 10-2019-0103186, filed 22 Aug. 2019 and 10-2020-0097398, filed on 4 Aug. 2020. The entire disclosures of the applications identified in this paragraph are incorporated herein by references.

TECHNICAL FIELD

The present disclosure relates to a composition for prevention or treatment of non-alcoholic steatohepatitis, the composition comprising, as an active ingredient, exosomes derived from mesenchymal stem cells differentiated from an induced pluripotent stem cell-derived mesenchymal stem cell progenitor treated with or without a pretreatment material.

BACKGROUND ART

Mesenchymal stem cells are stromal cells that can differentiate into various cells including osteoblast cells, chondrocytes, muscular cells, adipocytes, etc. Being capable of differentiate into various connective tissues such as cartilages, bone tissues, ligaments, marrow stromal cells, etc., mesenchymal stem cells have been studied for use in treating various diseases including arthritis, soft tissue defects caused by trauma and burn, and so on.

In recent years, active research has been ongoing into therapeutic effects of exosomes secreted from mesenchymal stem cells, but not mesenchymal stem cells themselves, on various diseases. For commercial availability, a large amount of quality exosomes is needed. However, only a small amount of exosomes can be obtained from mesenchymal stem cells. In addition, mesenchymal stem cells decrease in function and proliferative ability with the repetition of passages. Thus, a need rises for the technology development to establish cells with excellent proliferation ability while having functionality equal to or superior to that of mesenchymal stem cells.

Meanwhile, non-alcoholic steatosis is characterized by the accumulation of triglycerides in hepatocytes without excessive intake of alcohols. Non-alcoholic steatosis continues to increase due to excessive nutrition associated with high-fat and high-carbohydrate intake in modern people. For obesity and diabetes, non-alcoholic steatosis is frequently observed, but various factors are known to be relevant to non-alcoholic steatosis. It is reported that 80% of adults with non-alcoholic steatosis develop metabolic diseases such as insulin-resistant diabetes and heart disease.

Non-alcoholic steatosis is classified into non-alcoholic simple steatosis and non-alcoholic steatohepatitis (NASH) with inflammation, and if left untreated for a long time, can be developed into serious liver diseases such as hepatitis, liver fibrosis, cirrhosis, etc. Non-alcoholic steatosis is characterized by the accumulation of fat (fat infiltration) in hepatocytes.

Non-alcoholic simple steatosis can progress into non-alcoholic steatohepatitis. In non-alcoholic steatohepatitis, the fat accumulation is associated with varying degrees of inflammation and scarring of the liver, and in many cases insulin resistance, dyslipidemia, and hypertension. Non-alcoholic steatohepatitis most often occurs in people with excess body weight, excess blood cholesterol and triglyceride levels, and/or insulin resistance.

Recently, with the increase in the number of non-alcoholic steatohepatitis patients along with the increase in the obese population, the therapy market of non-alcoholic steatohepatitis has developed on a huge scale. Revelation of the incidence causes and mechanisms of non-alcoholic steatohepatitis has focused keen interest on the development of therapies for non-alcoholic steatohepatitis. However, safe and long-term allowable therapeutic agents for non-alcoholic steatohepatitis still remain insignificantly developed.

For treatment of non-alcoholic steatohepatitis, therapeutic agents for obesity, insulin tolerance, or hyperlipidemia, hepatoprotectants, and antioxidants are usually used. However, these medications are not essential treatments for non-alcoholic steatohepatitis, but are used as symptom improvement agents and have side effects when taken for a long time.

Therefore, there is a growing demand for the development of a safer, long-term allowable, novel therapeutic composition suitable for the treatment of the chronic disease non-alcoholic steatohepatitis.

DETAILED DESCRIPTION

Technical Problem

Leading to the present disclosure, intensive and thorough research, conducted by the present inventors, into the development of a therapeutic agent using exosomes of mesenchymal stem cells to treat non-alcoholic steatohepatitis, resulted in establishing induced pluripotent stem cell (iPSC)-derived mesenchymal stem cells differentiated from progenitor cells thereof and finding that exosomes derived from induced pluripotent stem cell (iPSC)-derived mesenchymal stem cells differentiated from the progenitor cells thereof which were pretreated with or without a pretreatment material exhibited excellent prophylactic and therapeutic effects on alcoholic steatohepatitis.

Therefore, an aspect of the present disclosure is to provide a pharmaceutical composition comprising exosomes isolated from induced pluripotent stem cell (iPSC)-derived mesenchymal stem cells (MSC) as an active ingredient for prevention or treatment of non-alcoholic steatohepatitis.

Another aspect of the present disclosure is to provide an exosome isolated from induced pluripotent stem cell-derived mesenchymal stem cells.

A further aspect of the present disclosure is to provide a pharmaceutical composition comprising exosomes isolated from induced pluripotent stem cell-derived mesenchymal stem cells (MSC) treated with a pretreatment material as an active ingredient for prevention or treatment of non-alcoholic steatohepatitis.

Still another aspect of the present disclosure is to provide exosomes isolated from induced pluripotent stem cell-derived mesenchymal stem cells wherein the exosomes are treated with a pretreatment material.

Technical Solution

The present inventors conducted intensive and thorough research into the development of a therapeutic agent using exosomes of mesenchymal stem cells to treat non-alcoholic steatohepatitis. As a culmination of the research, induced pluripotent stem cell (iPSC)-derived mesenchymal stem cells were established by differentiation from progenitor cells thereof and it was found that exosomes derived from induced pluripotent stem cell (iPSC)-derived mesenchymal stem cells differentiated from their progenitor cells treated with or without a pretreatment material exhibited excellent prophylactic and therapeutic effects on alcoholic steatohepatitis.

The present disclosure relates to an exosome isolated from induced pluripotent stem cell-derived mesenchymal stem cells differentiated from their progenitor cells and a pharmaceutical composition comprising the same as an active ingredient for prevention or treatment of non-alcoholic steatohepatitis, and to an exosome isolated from induced pluripotent stem cell-derived mesenchymal stem cells differentiated from their progenitor cells pretreated with a pretreatment material and a pharmaceutical composition comprising the same as an active ingredient for prevention or treatment of non-alcoholic steatohepatitis Below, a detailed description will be given of the present disclosure.

An aspect of the present disclosure pertains to a composition comprising exosomes isolated from induced pluripotent stem cell (iPSC)-derived mesenchymal stem cells (MSC) as an active ingredient for prevention or treatment of non-alcoholic steatohepatitis.

Another aspect of the present disclosure pertains to a composition comprising exosomes isolated from induced pluripotent stem cell-derived mesenchymal stem cells as an active ingredient for prevention, alleviation, amelioration, or treatment of non-alcoholic steatohepatitis.

As used herein, the term "non-alcoholic steatohepatitis" refers to a form of nonalcoholic fatty liver disease (NAFLD), a progressive liver disease characterized by fatty liver with inflammation or fibrosis, which is a precursor disease leading eventually to cirrhosis or liver cancer.

As used herein, the term "stem cells" refers to undifferentiated cells that can differentiate into two or more different types of cells and retain self-renewal performance. The stem cells of the present disclosure may be autologous or homologous stem cells.

The term "induced pluripotent stem cells", as used herein, refers to cells that have been reprogrammed back into an undifferentiated state of pluripotency by inducing dedifferentiation in already differentiated cells such as somatic cells.

The differentiation can be induced by introducing and expressing specific genes (e.g., Sox2, c-Myc, Klf4, Oct-4, etc.) or injecting dedifferentiation inducing proteins expressed in the cells having the specific genes introduced thereinto.

Pluripotency is defined as the potential to differentiate into tissues or organs of any origin of the three germ layers endoderm, mesoderm, and ectoderm.

As used herein, the term "mesenchymal stem cells" refers to pluripotent stem cells capable of differentiating into various types of cells including osteoblasts, chondrocytes, myocytes, lipocytes, etc. The mesenchymal stem cells may be usually bone marrow-derived mesenchymal stem cells, but may be derived from umbilical cord, umbilical cord blood, adipose tissues, amniotic fluid, or molar tooth buds. Mesenchymal stem cells are also called stromal cells.

The mesenchymal stem cell progenitor is not a progenitor of general mesenchymal stem cells, but a progenitor of the mesenchymal stem cells derived from the induced pluripotent stem cell (iPSC) [developed by the present inventors].

In the present disclosure, the induced pluripotent stem cell-derived mesenchymal stem cell progenitor may not express SSEA-4 (stage-specific embryonic antigen 4) protein.

In the present disclosure, the induced pluripotent stem cell-derived mesenchymal stem cells may be derived from a progenitor of induced pluripotent stem cell-derived mesenchymal stem cells which does not express SSEA-4 (stage-specific embryonic antigen 4) protein.

The "induced pluripotent stem cell", as used herein, refers to cells which have been induced to have pluripotency by artificial dedifferentiation from differentiated cells and is also known as dedifferentiated stem cells.

The artificial dedifferentiation process is performed by introduction of a dedifferentiation factor through viral mediation using retrovirus, lentivirus, and Sendai virus or through non-viral mediation using a non-viral vector, a protein, and a cell extract, or by a stem cell extract, a compound, etc.

The induced pluripotent stem cells have almost the same traits as embryonic stem cells, specifically are similar in cell morphology and gene and protein expression patterns, exhibits pluripotency in vitro and in vivo, and develop teratoma. When the induced pluripotent stem cells were inserted into mouse blastocysts, chimeric mice were generated with germ line transmission observed therein.

The induced pluripotent stem cells of the present disclosure are intended to encompass induced pluripotent stem cells derived from all mammals such as humans, monkeys, pigs, horses, cows, sheep, dogs, cats, mice, rabbits, and so on, with preference for human-derived induced pluripotent stem cells.

In addition, the somatic cells from which the induced pluripotent stem cells of the present disclosure are dedifferentiated may be somatic cells derived from umbilical cord, umbilical cord blood, bone marrow, fat, muscle, nerve, skin, amniotic membrane, amniotic fluid, or placenta, but with no limitations thereto.

Concrete examples of the somatic cells include fibroblasts, hepatocytes, adipose cells, epithelial cells, epidermal cells, chondrocytes, muscle cells, cardiac muscle cells, melaonocytes, neural cells, glial cells, astroglial cells, monocytes, and macrophages, but are not limited thereto.

In an embodiment of the present disclosure, the mesenchymal stem cells of the present disclosure express at least one gene selected from the group consisting of ANKRD1, CPE, NKAIN4, LCP1, CCDC3, MAMDC2, CLSTN2, SFTA1P, EPB41L3, PDE1C, EMILIN2, SULT1C4, TRIM58, DENND2A, CADM4, AIF1L, NTM, SHISA2, RASSF4, and ACKR3 at a higher level, compared to the same number of other mesenchymal stem cells.

In another embodiment of the present disclosure, the mesenchymal stem cells of the present disclosure express at least one gene selected from the group consisting of DHRS3, BMPER, IFI6, PRSS12, RDH10, and KCNE4 at a lower level, compared to the same number of other mesenchymal stem cells.

The mesenchymal stem cells and the other mesenchymal stem cells used in the same number are derived from allogeneic tissues. In greater detail, the mesenchymal stem cells are progenitor cells of induced pluripotent stem cell-derived mesenchymal stem cells.

In an embodiment of the present disclosure, the mesenchymal stem cells are mesenchymal stem cells derived from induced pluripotent stem cells of umbilical cord tissues and the other mesenchymal stem cells used in the same number as a comparison are mesenchymal stem cells derived from umbilical cord tissues.

In the present disclosure, the mesenchymal stem cells differentiated from the induced pluripotent stem cell-derived mesenchymal stem cell progenitor are designated BxC (Br-exogen stem cells). Herein, the term "induced pluripotent stem cell-derived mesenchymal stem cells (BxC)" is also expressed as "induced pluripotent stem cell-derived mesenchymal cells".

As used herein, the term "induced pluripotent stem cell-derived mesenchymal stem cell progenitor" refers to cells in the stage just before induced pluripotent stem cells are not differentiated completely into mesenchymal stem cells, which are a kind of induced pluripotent stem cell-derived mesenchymal stem cells, and means cells that do not express SSEA-4 protein and become complete mesenchymal stem cells through further culturing.

The induced pluripotent stem cell-derived mesenchymal stem cells (BxC) according to the present disclosure show no different karyotypes and a higher growth potential, compared to mesenchymal stem cells (MSC) derived from the same tissue (e.g., umbilical cord). For instance, BxC of the present disclosure after undergoing 9 or more passages, exhibits a growth potential 10 or more times greater than that of mesenchymal stem cells (MSC) derived from the same tissue and no reduction in growth potential is observed in BxC in spite of 12 or more passages. In addition, BxC is observed to express the growth potential-related marker Ki67 at a level two or more folds higher than MSC.

The induced pluripotent stem cell-derived mesenchymal stem cells (BxC) release massive amounts of functional proteins, such as endostatin, endothelin-1, VEGF-A, thrombospondin-2, PIGF, PDGF-AA, beta-NGF, and HB-EGF, compared to the same number of mesenchymal stem cells.

Herein, endostatin is a naturally occurring, 20-kDa C-terminal fragment derived from type XVIII collagen. It is reported to serve as an anti-angiogenic agent.

Endothelin-1, also known as preproendothelin-1 (PPET1), is a potent vasoconstrictor that is encoded by the EDN1 gene and produced by vascular endothelial cells.

Vascular endothelial growth factor A (VEGF-A) is a protein that is encoded by the VEGFA gene and is known to induce vascular growth through its interactions with the VEGFR1 and VEGFR2 receptors found in prominently on the endothelial cell membrane.

Thrombospondin-2 is a protein that is encoded by the THBS2 gene and mediates cell-to-cell and cell-to-matrix interactions. The role of the protein in cancer is controversial. Studies of the mouse counterpart suggest that this protein may modulate the cell surface properties of mesenchymal cells and be involved in cell adhesion and migration.

PIGF (placental growth factor) is a protein that is encoded by the PGF gene. The protein is a member of the VEGF sub-family and plays a key role in angiogenesis and vasculogenesis during embryogenesis.

PDGF-AA (platelet-derived growth factor) is a growth factor that regulates cell growth and division. In particular, the growth factor plays a significant role in blood vessel formation, growth, and proliferation, chemotaxis, and migration of mesenchymal stem cells.

NGF (nerve growth factor) is a neurotrophic factor and neuropeptide primarily involved in the regulation of growth, maintenance, proliferation, and survival of certain target neurons. NGF is a complex of three proteins—alpha-NGF, beta-NGF, and gamma-NGF at 2:1:2 ratio when expressed. The gamma subunit of this complex acts as a serine protease, and cleaves the N-terminal of the beta subunit, thereby activating the protein into functional NGF.

HB-EGF (heparin-binding EGF-like growth factor) is a member of the EGF family of proteins that is encoded by the HBEGF gene. HB-EGF has been shown to play an important role in heart development and vascular distribution and serves as an essential protein for the epithelialization required for cutaneous wound healing.

As used herein, the term "exosome" refers to a membrane vesicle that is extracellularly secreted from a cell or has a membrane structure composed of a lipid-bilayer present in the cell, and exosomes are found in the body fluid of almost all eukaryotes. Exosomes are about 30 to 1000 nm in diameter. Cells release exosomes directly from cell membranes when multivesicular bodies are fused to cell membranes. It is well known that exosomes play a functional role in mediating coagulation, cell-cell communication, and cellular immunity by transporting intracellular biomolecules, such as proteins, bioactive lipids, and RNA (miRNA).

In the present disclosure, the exosomes are intended to encompass microvesicles. CD63 and CD81 are known as marker proteins of exosomes. In addition, various proteins including, for example, cell surface receptors such as EGFR, signaling-related molecules, cell adhesion-related proteins, MSC-associated antigens, heat shock proteins, and vesiculation-related Alix are found in exosomes.

In the present disclosure, exosomes isolated from the induced pluripotent stem cell-derived mesenchymal stem cells refer to exosomes found within the induced pluripotent stem cell-derived mesenchymal stem cells (BxC) or released from BxC.

In the present disclosure, the exosomes isolated from the induced pluripotent stem cell-derived mesenchymal stem cells may be those isolated from mesenchymal stem cells differentiated from progenitor cells of induced pluripotent stem cell-derived mesenchymal stem cells that do not express SSEA-4 (stage-specific embryonic antigen 4) protein.

As used herein, the term "comprising as an active ingredient" refers to comprising exosomes isolated from the induced pluripotent stem cell-derived mesenchymal stem cells in an amount sufficient to attain activity to prevent or treat non-alcoholic steatohepatitis.

In the present disclosure, the pharmaceutical composition may comprise exosomes isolated from induced pluripotent stem cell-derived mesenchymal stem cells in an amount of 1 to 10,000 μg, 1 to 1,000 μg, 10 to 10,000 μg, 10 to 1,000 μg, 100 to 10,000 μg, 100 to 1,000 μg, 50 to 10,000 μg, 50 to 1,000 μg, or 50 to 500 μg as calculated for exosome protein, but with no limitations thereto.

As used herein, the term "prevention" refers to all acts of suppressing non-alcoholic steatohepatitis or delaying the progress of non-alcoholic steatohepatitis by administering the composition of the present disclosure.

As used herein, the term "treatment" refers to (a) suppressing the development of non-alcoholic steatohepatitis; (b) alleviating non-alcoholic steatohepatitis; and (c) removing non-alcoholic steatohepatitis.

In addition to the active ingredient, the pharmaceutical composition of the present disclosure comprises a pharmaceutically acceptable carrier. So long as it is typically used for preparing a pharmaceutical composition, any pharmaceutically acceptable carrier may be contained in the pharmaceutical composition of the present disclosure. Examples of the pharmaceutically acceptable carrier include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil, but are not limited thereto. In addition to the above ingredients, the pharmaceutical composition of the present disclosure may further comprise a lubricant, a humectant, a sweetener, a flavoring agent, an emulsifier, a suspending agent, a preservative, and the like.

The pharmaceutical composition may be administered orally or parenterally (e.g., intravenously, subcutaneously, intraperitoneally, or intralesionally) depending on a desired method. A dose may vary depending on various factors including the patient's states and body weight, severity of diseases, formulation types, administration route, and administration time and may be properly selected by a person skilled in the art.

The pharmaceutical composition may be administered in a pharmaceutically effective amount. Herein, the term "pharmaceutically effective amount" means an amount sufficient to treat the disease at a reasonable benefit/risk ratio applicable to medical treatment. The effective amount may be determined based on a type of a patient's disease, severity thereof, activity of the drug, sensitivity to the drug, an administration time, an administration route and a discharge rate, a treatment duration, a drug used concurrently, and other factors well known in the medical field.

The composition according to the present disclosure may be administered as an individual therapeutic agent alone or in combination with other therapeutic agents. In the latter case, administration may be conducted sequentially or simultaneously. Also, the composition may be administered at a single dose or at divided multiple doses. Considering all of the above factors, it is important to administer a minimal amount capable of achieving the maximum effect without side effects. The appropriate amount may be easily determined by a person skilled in the art.

Specifically, the effective amount of the pharmaceutical compound according to the present disclosure may vary depending on the patient's age, sex and weight, the absorptivity, inactivation rate, and discharge rate of the active ingredient in vivo, types of disease, and drugs used in combination.

Another aspect of the present disclosure pertains to exosomes isolated from the induced pluripotent stem cell-derived mesenchymal stem cells.

The exosomes (BxC-e) isolated from induced pluripotent stem cell-derived mesenchymal stem cells differentiated from their progenitor cells retain the traits of exosomes themselves. As will be proven in the Examples below, the exosomes isolated from progenitor cells of induced pluripotent stem cell-derived mesenchymal stem cells has excellent inhibitory activity against differentiation into lipids (FIG. 2). In addition, BxC-e according to the present disclosure was found to suppress lipogenesis and inflammation as well as endoplasmic reticulum stress in steatosis-induced hepatocytes (FIGS. 5 to 7).

Another aspect of the present disclosure pertains to a method for treatment of non-alcoholic steatohepatitis, the method comprising a step of administering, to a subject, exosomes isolated from the induced pluripotent stem cell-derived mesenchymal stem cells.

The term "subject" means a target in need of treatment of the disease and is intended to encompass humans or non-human primates, and mammals such as mice, dogs, cats, horses, and cows.

Another aspect of the present disclosure pertains to a use of exosomes isolated from the induced pluripotent stem cell-derived mesenchymal stem cells for treating non-alcoholic steatohepatitis.

Since the method and use for treatment of non-alcoholic steatohepatitis has constituents in common with the exosomes isolated from induced pluripotent stem cell-derived mesenchymal stem cells and the pharmaceutical composition comprising the same according to the present disclosure, the common content therebetween is omitted from the description in order to avoid too much excessive complexity.

Another aspect of the present disclosure pertains to a pharmaceutical composition comprising exosomes isolated from induced pluripotent stem cell (induced pluripotent stem cell, iPSC)-derived mesenchymal stem cells (MSC) pretreated with a pretreatment material as an active ingredient for prevention or treatment of non-alcoholic steatohepatitis.

In the present disclosure, the induced pluripotent stem cell-derived mesenchymal stem cells may be those differentiated from progenitor cells of induced pluripotent stem cell-derived mesenchymal stem cells that do not express SSEA-4 (stage-specific embryonic antigen 4) protein.

As used herein, the term "pretreatment" refers to a process of contacting progenitor cells of induced pluripotent stem cell-derived mesenchymal stem cells with a cell culture medium containing a pretreatment material during culturing of the progenitor cells.

The pretreatment may be conducted by culturing the induced pluripotent stem cell-derived mesenchymal stem cells in a cell culture medium containing a pretreatment material.

Any cell culture medium for animal cells may be available. For example, DMEM (Dulbecco's modification of Eagle's medium), a mixture of DMEM and F12, Eagle's MEM (Eagle's minimum essential medium), α-MEM, Iscove's MEM, 199 medium, CMRL 1066, RPMI 1640, F12, F10, Way-mouth's MB752/1, McCoy's 5A, and MCDB series may be employed.

The culturing may be carried out for 6 to 48 hours.

Specifically, the culturing may be carried out for 6 to 42 hours, 6 to 36 hours, 6 to 30 hours, 6 to 27 hours, 12 to 48 hours, 12 to 42 hours, 12 to 36 hours, 12 to 30 hours, 12 to 27 hours, 18 to 48 hours, 18 to 42 hours, 18 to 36 hours, 18 to 30 hours, 18 to 27 hours, 21 to 48 hours, 21 to 42 hours, 21 to 36 hours, 21 to 30 hours, or 21 to 27 hours.

The pretreatment material may be 1-(6-benzothiazolylsulfonyl)-5-chloro-1H-indole-2-butanoic acid or exendin-4.

1-(6-Benzothiazolylsulfonyl)-5-chloro-1H-indole-2-butanoic acid, named "Lanifibranor", is an agonist of peroxisome proliferator-activated receptors (PPARs).

Lanifibranor may be contained at a concentration of 1 to 100 μM in the cell culture medium.

Specifically, Lanifibranor may be contained at a concentration of 1 to 90 μM, 1 to 80 μM, 1 to 70 μM, 1 to 60 μM, 1 to 50 μM, 1 to 40 μM, 1 to 30 μM, 10 to 90 μM, 10 to 80 μM, 10 to 70 μM, 10 to 60 μM, 10 to 50 μM, 10 to 40 μM, and 10 to 30 μM in the cell culture medium.

In an embodiment of the present disclosure, lanifibranor may be added at a concentration of 1 to 1,000 μM, 1 to 500 μM, 1 to 100 μM, 1 to 90 μM, 1 to 80 μM, 1 to 70 μM, 1 to 60 μM, 1 to 50 μM, 1 to 40 μM, 1 to 30 μM, 1 to 20 μM, or 10 μM to the medium, but with no limitations thereto.

In an embodiment of the present disclosure, exosomes may be those isolated from progenitor cells of induced pluripotent stem cell-derived mesenchymal stem cells, cultured in a medium containing 1-(6-benzothiazolylsulfonyl)-

5-chloro-1H-indole-2-butanoic acid at a concentration of 1 to 1000 µM, 1 to 500 µM, 1 to 100 µM, 1 to 90 µM, 1 to 80 µM, 1 to 70 µM, 1 to 60 µM, 1 to 50 µM, 1 to 40 µM, 1 to 30 µM, 1 to 20 µM, 10 to 90 µM, 10 to 80 µM, 10 to 70 µM, 10 to 60 µM, 10 to 50 µM, 10 to 40 µM, 10 to 30 µM, or 10 µM.

Exendin-4, which is a peptide agonist of the glucagon-like peptide (GLP) receptor, stimulates insulin release and has clinically used for treatment of type 2 diabetes mellitus and Parkinson's disease.

Exendin-4 may be contained at a concentration of 1 to 100 nM in the cell culture medium.

Specifically, the cell culture medium may contain exendin-4 at a concentration of 1 to 90 nM, 1 to 80 nM, 1 to 70 nM, 1 to 60 nM, 1 to 50 nM, 1 to 40 nM, 1 to 30 nM, 10 to 90 nM, 10 to 80 nM, 10 to 70 nM, 10 to 60 nM, 10 to 50 nM, 10 to 40 nM, 10 to 30 nM, or 20 nM.

In an embodiment of the present disclosure, exosomes may be those isolated from induced pluripotent stem cell-derived mesenchymal stem cells cultured in a medium containing exendin-4 at a concentration of 1 to 90 nM, 1 to 80 nM, 1 to 70 nM, 1 to 60 nM, 1 to 50 nM, 1 to 40 nM, 1 to 30 nM, 10 to 90 nM, 10 to 80 nM, 10 to 70 nM, 10 to 60 nM, 10 to 50 nM, 10 to 40 nM, 10 to 30 nM, or 20 nM, but with no limitations thereto.

The pharmaceutical composition of the present disclosure may comprise exosomes isolated from progenitor cells of induced pluripotent stem cell-derived mesenchymal stem cells in an amount of 1 to 10,000 µg, 1 to 1,000 µg, 10 to 10,000 µg, 10 to 1,000 µg, 100 to 10,000 µg, 100 to 1,000 µg, 50 to 10,000 µg, 50 to 1,000 µg, or 50 to 500 µg as calculated for exosome protein, but with no limitations thereto, the progenitor cells being pretreated with 1-(6-benzothiazolylsulfonyl)-5-chloro-1H-indole-2-butanoic acid.

The pharmaceutical composition of the present disclosure may comprise exosomes isolated from progenitor cells of induced pluripotent stem cell-derived mesenchymal stem cells in an amount of 1 to 10,000 µg, 1 to 1,000 µg, 10 to 10,000 µg, 10 to 1,000 µg, 100 to 10,000 µg, 100 to 1,000 µg, 50 to 10,000 µg, 50 to 1,000 µg, or 50 to 500 µg, but with no limitations thereto, the progenitor cells being pretreated with exendin-4.

Another aspect of the present disclosure pertains to exosomes isolated from induced pluripotent stem cell-derived mesenchymal stem cells treated with a pretreatment material.

The exosomes (BxC-V37e and BxC-G63e) isolated from induced pluripotent stem cell-derived mesenchymal stem cells treated with a pretreatment material according to the present disclosure retain the traits of exosomes themselves. As will be proven in the Examples below, BxC-V37e and BxC-G63e according to the present disclosure inhibit lipogenesis, inflammation, and endoplasmic reticulum stress in steatosis-induced hepatocytes (FIGS. 5 to 10).

Another aspect of the present disclosure pertains to a food composition for alleviating, suppressing, or ameliorating non-alcoholic steatohepatitis, the composition comprising exosomes isolated from induced pluripotent stem cell-derived mesenchymal stem cells.

Another aspect of the present disclosure pertains to a food composition for alleviating, suppressing, or ameliorating non-alcoholic steatohepatitis, the food composition comprising exosomes isolated from induced pluripotent stem cell-derived mesenchymal stem cells pretreated with a pretreatment material.

Since the food composition according to the present disclosure has constituents in common with the exosomes isolated from induced pluripotent stem cell-derived mesenchymal stem cells and the pharmaceutical composition comprising the same according to the present disclosure, the common content therebetween is omitted from the description in order to avoid excessive complexity.

The food composition according to the present disclosure may further contain ingredients typically used in foods, for example, proteins, carbohydrates, lipids, nutrients, condiments, and flavoring agents, but with no limitations thereto.

The natural carbohydrates that can be contained in the food composition according to the present disclosure may include monosaccharides such as glucose and fructose, disaccharides such as maltose and sucrose, oligosaccharides, polysaccharides such as dextrin and cyclodextrin, and sugar alcohols such as xylitol, sorbitol and erythritol, but are not limited thereto.

The flavoring agent that can be used in the food composition according to the present disclosure may include a natural flavoring agent, such as thaumatin, a stevia extract, etc., and a synthetic flavoring agent such as saccharin or aspartame, but is not limited thereto.

An aspect of the present disclosure is directed to a method for treating non-alcoholic steatohepatitis, the method comprising a step of administering, to a subject, exosomes isolated from induced pluripotent stem cell-derived mesenchymal stem cells pretreated with the pretreatment material.

The term "subject" means a target in need of treatment of the disease and is intended to encompass humans or non-human primates, and mammals such as mice, dogs, cats, horses, and cows.

Another aspect of the present disclosure pertains to a use of exosomes for treating non-alcoholic steatohepatitis, the exosomes being isolated from the induced pluripotent stem cell-derived mesenchymal stem cells pretreated with the pretreatment material.

Since the method and use for treatment of non-alcoholic steatohepatitis has constituents in common with the exosomes isolated from induced pluripotent stem cell-derived mesenchymal stem cells pretreated with a pretreatment material and the pharmaceutical composition comprising the same according to the present disclosure, the common content therebetween is omitted from the description in order to avoid too much excessive complexity.

Advantageous Effects

The present disclosure relates to a pharmaceutical composition for prevention or treatment of non-alcoholic steatohepatitis, the composition comprising, as an active ingredient, exosomes isolated from induced pluripotent stem cell-derived mesenchymal stem cells which have been or have not been treated with a pretreatment material. The exosomes of the present disclosure exhibit a more improved effect of preventing or treating non-alcoholic steatohepatitis, compared to those isolated from conventional mesenchymal stem cells and as such, can be advantageously used for relevant research and development, and productization.

BEST MODE FOR CARRYING OUT THE INVENTION

The present disclosure is concerned with a pharmaceutical composition comprising exosomes isolated from induced pluripotent stem cell (iPSC)-derived mesenchymal stem cells (MSC) as an active ingredient for prevention, allevia-tion, inhibition, or treatment of non-alcoholic steatohepati-tis.

Detailed Description

Hereinafter, the present disclosure will be described in detail with reference to examples. These examples are only for illustrating the present disclosure more specifically, and it will be apparent to those skilled in the art that the scope of the present disclosure is not limited by these examples.

Throughout the description, the term "%" used to express the concentration of a specific material, unless otherwise particularly stated, refers to (wt/wt) % for solid/solid, (wt/vol) % for solid/liquid, and (vol/vol) % for liquid/liquid.

Preparation Example: Isolation and Culturing of Induced Pluripotent Stem Cell (iPSC)-Derived Mesenchymal Stem Cell (BxC)

First, induced pluripotent stem cells (iPSC) were cultured for 7 days in DMEM supplemented with 10% FBS and 10 ng/ml bFGF. From the cultured induced pluripotent stem cells, SSEA-4 (−) cells that did not express SSEA-4 (stage-specific embryonic antigen 4) protein were separated as progenitor cells of induced pluripotent stem cell-derived mesenchymal stem cells by FACS. The separated SSEA-4 (−) cells were additionally cultured for 7 days in the same medium by passage to obtain induced pluripotent stem cell-derived mesenchymal stem cells according to the pres-ent disclosure. The induced pluripotent stem cell-derived mesenchymal stem cells were named BxC (Brexogen stem cells).

The induced pluripotent stem cell-derived mesenchymal stem cells, named BxC, were further cultured in a culture medium [high glucose DMEM (Gibco, Cat no. 11995-065), 10% Fetal bovine Serum (HyClone), 1% MEM Non-Essen-tial Amino Acids Solution (100×) (Gibco, Cat no. 11140-050)].

Example 1: Isolation of Exosomes (BxC-e) from Induced Pluripotent Stem Cell-Derived Mesenchymal Stem Cells (BxC)

The induced pluripotent stem cell-derived mesenchymal stem cells (hereinafter referred to as "BxC") culture obtained in Preparation Example was collected and centri-fuged at 300×g for 10 minutes to remove the cells and cell debris. The supernatant was filtered through a 0.22-μm filter and then centrifuged at 10000×g and 4° C. for 70 minutes in a high-speed centrifuge. The supernatant thus obtained was centrifuged at 100,000×g and 4° C. for 90 minutes in an ultracentrifuge to obtain exosomes as a pellet. The exosomes were diluted in phosphate buffered saline (PBS) before subsequent experiments.

Experimental Example 1: Characterization of Exosomes (BxC-e) Isolated from Induced Pluripotent Stem Cell-Derived Mesenchymal Stem Cells The exosomes isolated in Example 1 (hereinafter referred to as "BxC-e") were analyzed for size distribution by nanoparticle tracking assay (NanoSight NS300, Malvern) and for morphology by electron microscopy.

Figure 1A:
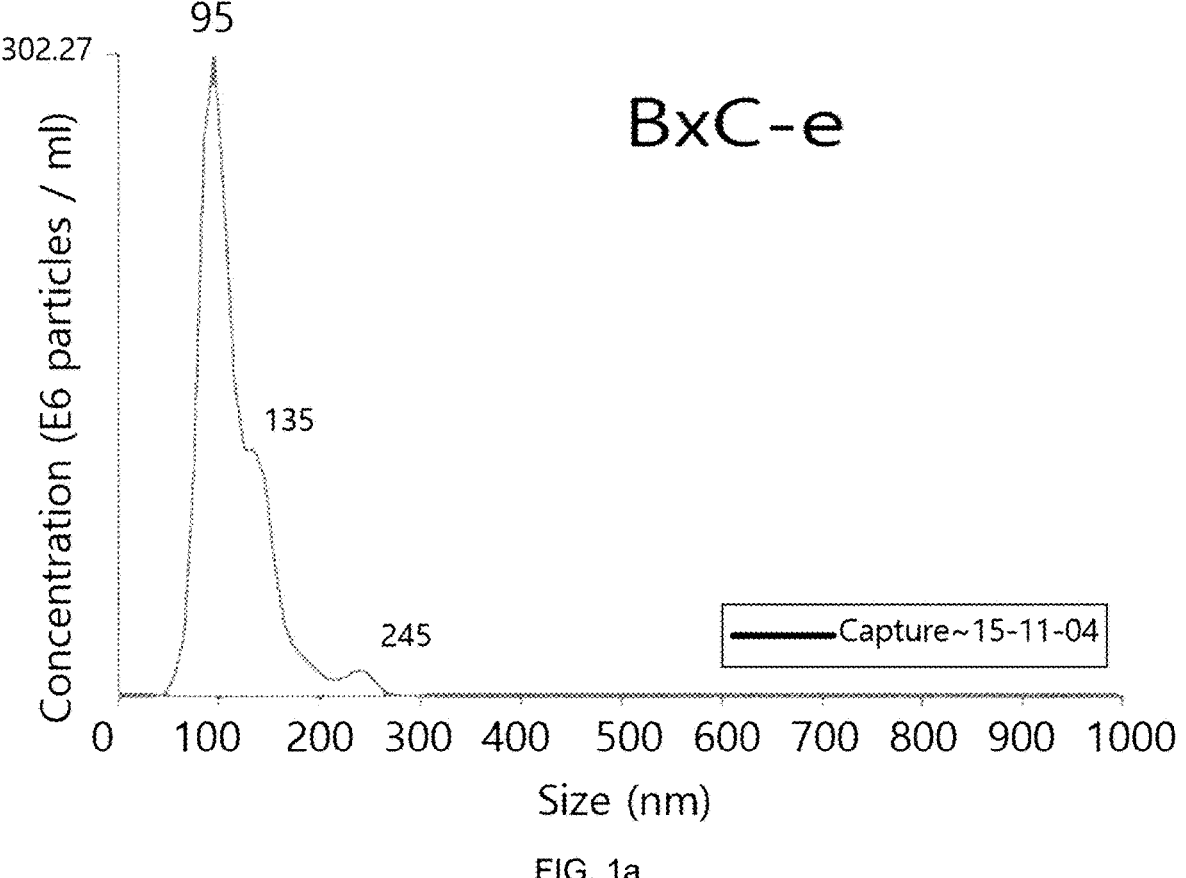
FIG. 1a is a graph showing the mean size and distribution of exosomes (BxC-e) isolated from induced pluripotent stem cell-derived mesenchymal stem cells (BxC).
Figure 1B:
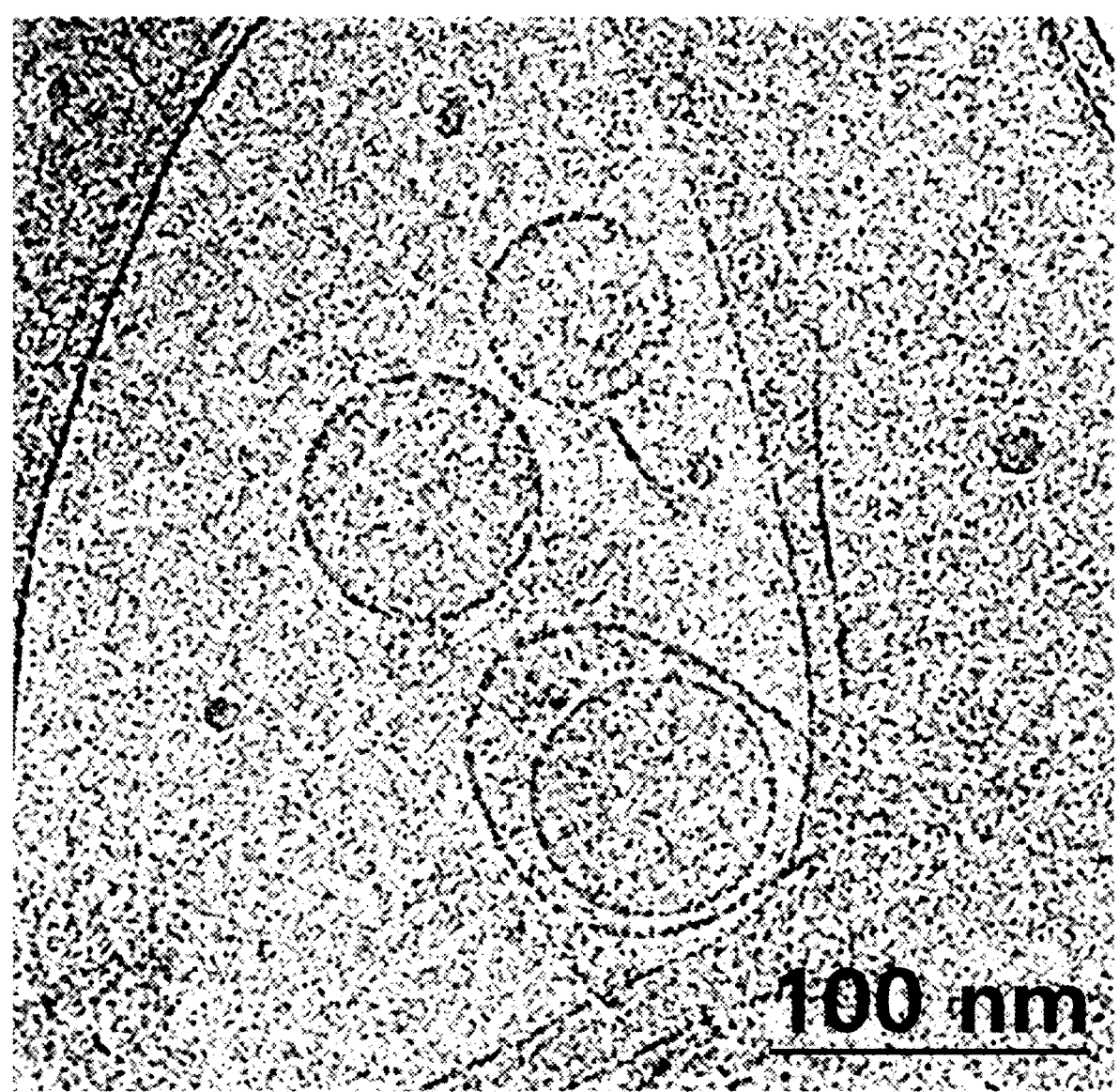
FIG. 1*b* is an electron microscopic image of exosomes (BxC-e) isolated from induced pluripotent stem cell-derived mesenchymal stem cells (BxC).

As can be seen in FIGS. 1a and 1b, the exosomes isolated from BxC according to the present disclosure retained the traits of exosome themselves.

Experimental Example 2: Inhibitory Effect of Exosomes (BxC-e) Isolated from Induced Pluripotent Stem Cell-Derived Mesenchymal Stem Cells on Adipose Differentiation The exosomes isolated in Example 1 was examined for an inhibitory effect on adipose differentiation.

Human adipocytes (primary human adipocyte, ATCC, USA) were seeded into 6-well plates and cultured at 37° C. in DMEM supplemented with 1% penicillin-streptomycin and 10% CS (Gibco, USA) in a 5% $CO_2$ incubator until growth to confluence (6 days at maximum).

After 6 days of incubation, the adipocytes were cultured for an additional 5 days in a base medium in which DMEM medium supplemented with 1% penicillin-streptomycin and 10% FBS (Gibco, USA) was mixed with a lipid differen-tiation medium [34 μM pantothenate (Sigma), 66 μM biotin (Sigma), 0.5 mM insulin (Sigma), 1 mM dexamethasone (Sigma), and 0.05 M IBMX (Sigma)]. Then, incubation was continued for an additional 9 days in a mixture of DMEM (Gibco, USA) and a lipid differentiation medium [34 μM pantothenate (Sigma), 66 μM biotin (Sigma), 0.5 mM insu-lin (Sigma), and 1 mM dexamethasone (Sigma)].

Adipocytes were cultured for 14 days in DMEM supple-mented with 10% FBS for use as a negative control, for 14 days in a lipid differentiation condition without BxC-e treatment for use as a vehicle control, and for 14 days in a lipid differentiation condition containing BxC-e for use as a BxC-e-treated group.

After complete removal of the culture medium, the cells were washed twice with PBS and fixed for 1 hour by adding a 10% formalin solution at a concentration of 400 μl/well. After washing with PBS, Oil-red O working solution was added at a concentration of 400 μl/well to stain lipids within adipocytes differentiated for 2 hours. Then, the Oil-red O working solution was aspirated and the residual Oil-red O working solution on walls of the wells was completely removed using secondary distilled water. The plates were dried for 5 minutes in a drier, followed by adding 500 μl of isopropyl alcohol to each well.

Absorbance was read at 490 nm on a microplate reader (Model 680 microplate reader, Bio-Rad, USA) to quantita-tively compare lipids.

Figure 2A:
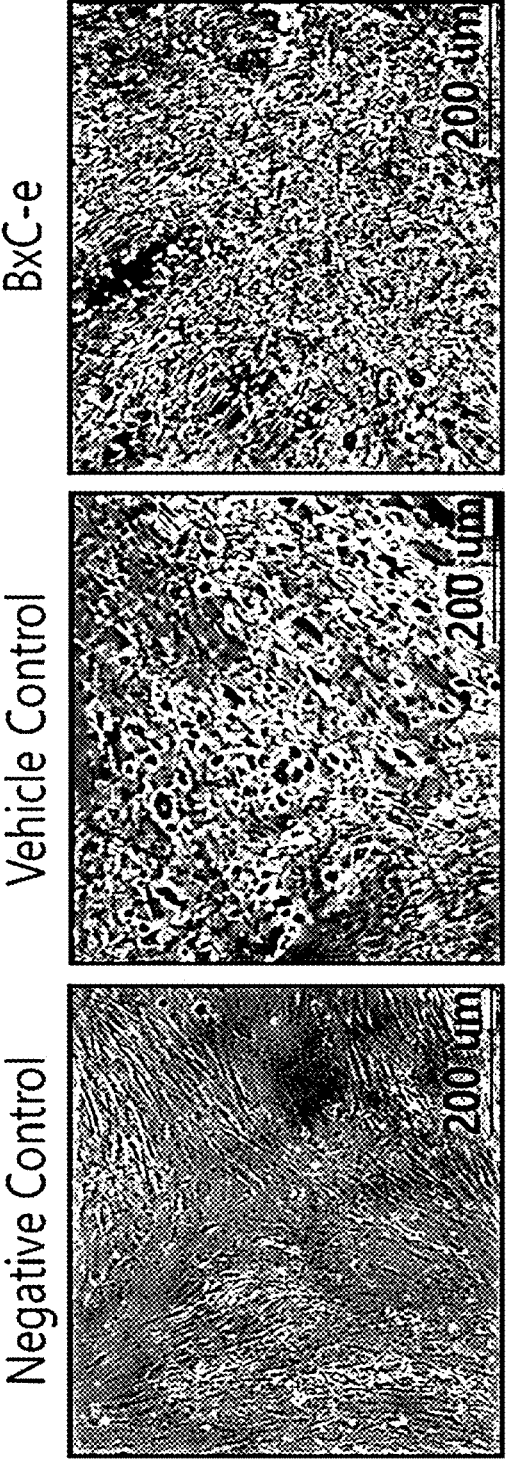
FIG. 2*a* shows microscopic images illustrating inhibitory effects of exosomes (BxC-e) isolated from induced pluripotent stem cell-derived mesenchymal stem cells (BxC) on lipogenesis.
Figure 2B:
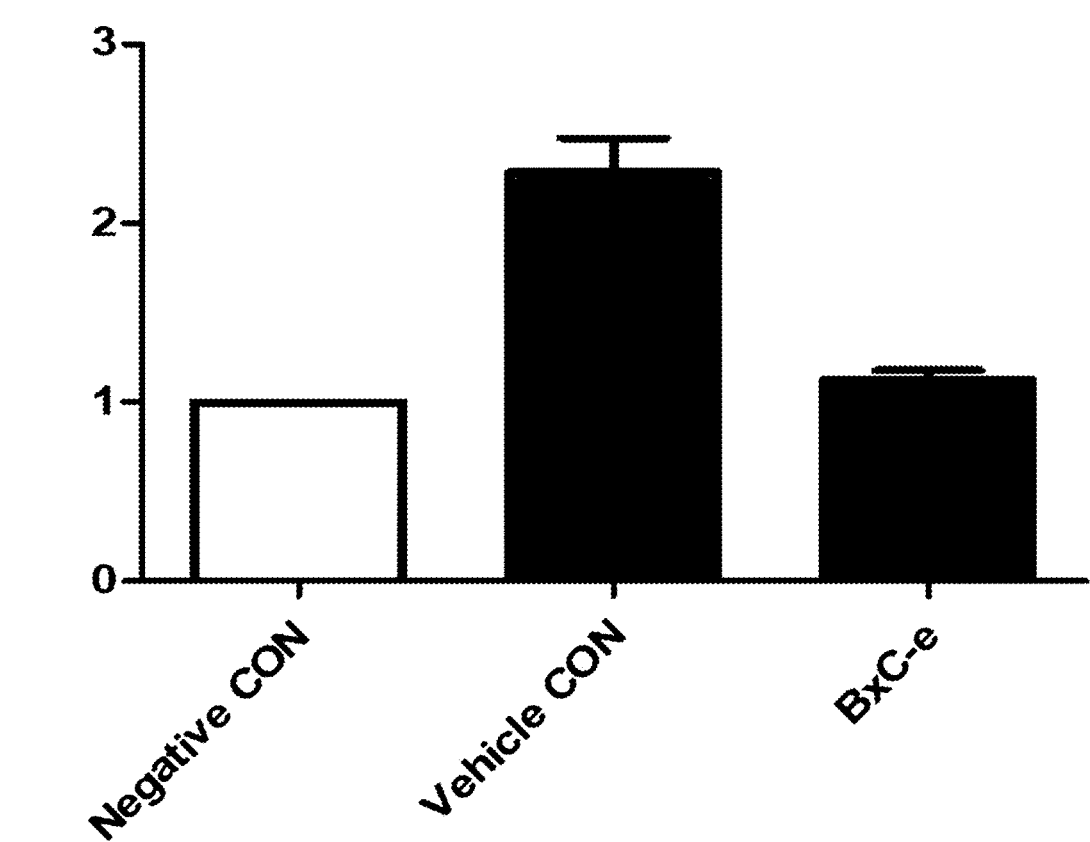
FIG. 2*b* is a graph illustrating inhibitory effects of exosomes (BxC-e) isolated from induced pluripotent stem cell-derived mesenchymal stem cells (BxC) on lipogenesis.
Figure 3A:
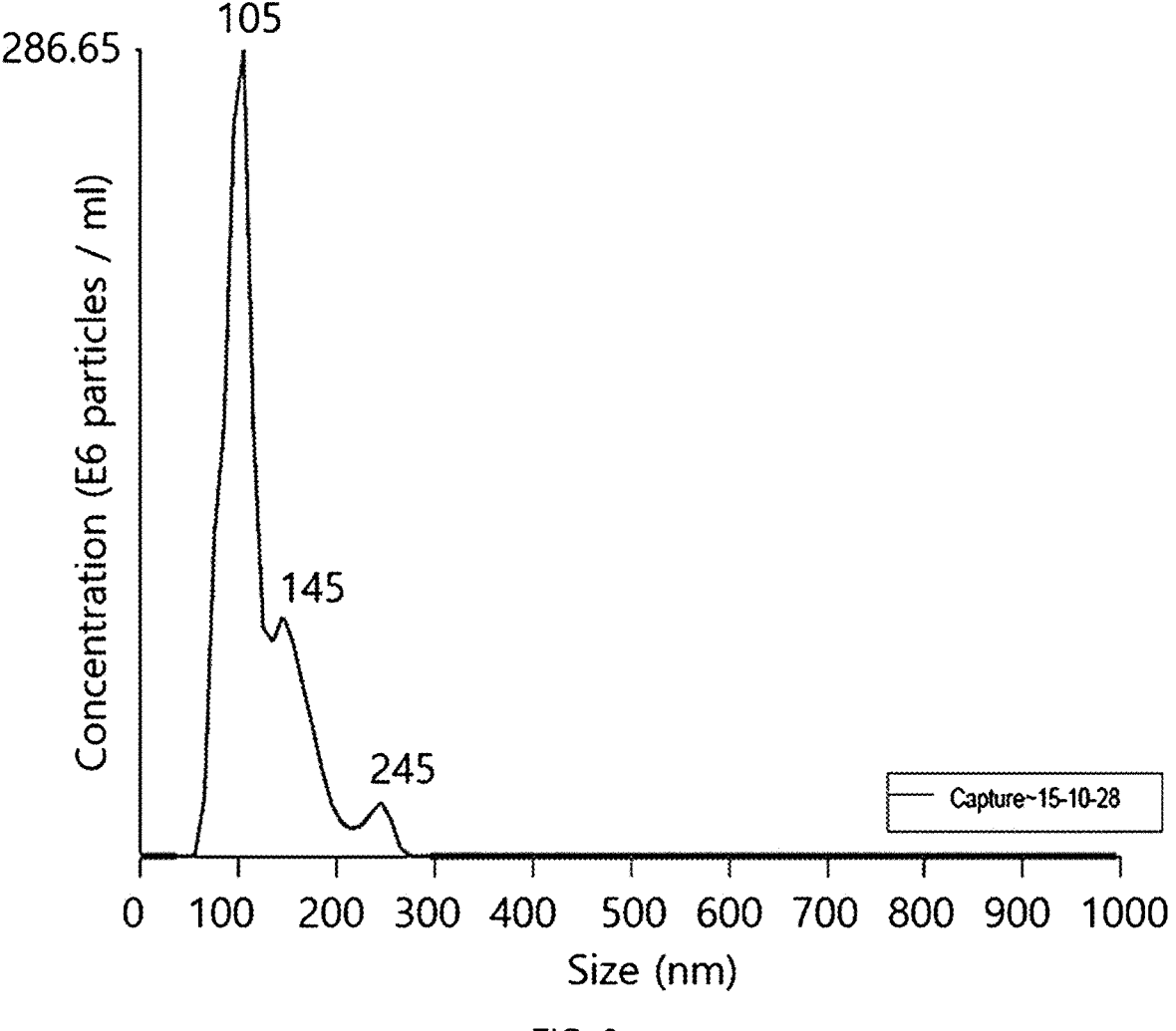
FIG. 3*a* is a graph showing the mean size and distribution of exosomes (BxC-V37e) isolated from induced pluripotent stem cell-derived mesenchymal stem cells (BxC) pretreated with LANIFIBRANOR.
Figure 3B:
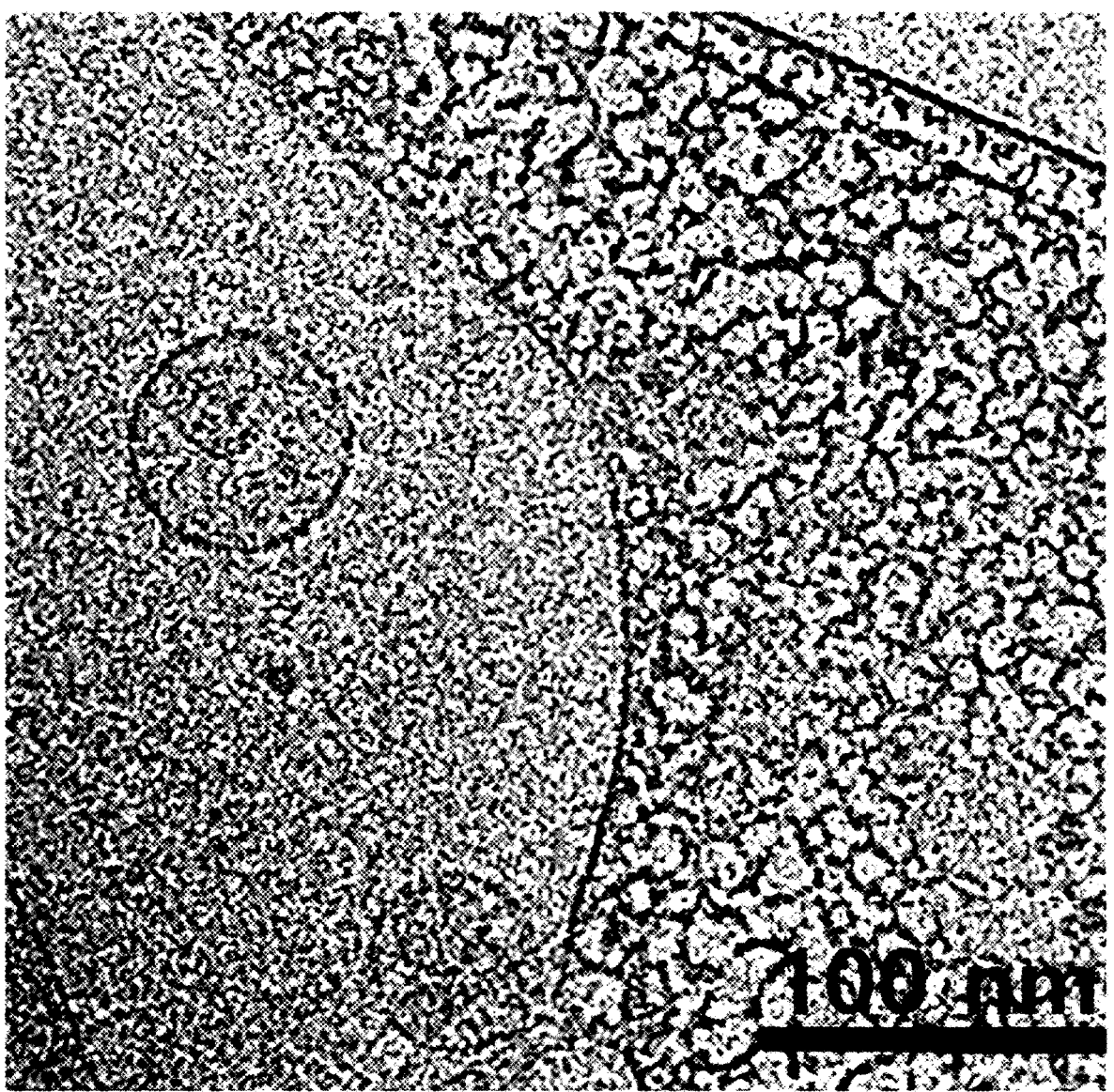
FIG. 3*b* is an electron microscopic image of exosomes (BxC-V37e) isolated from induced pluripotent stem cell-derived mesenchymal stem cells (BxC) pretreated with LANIFIBRANOR.
Figure 4A:
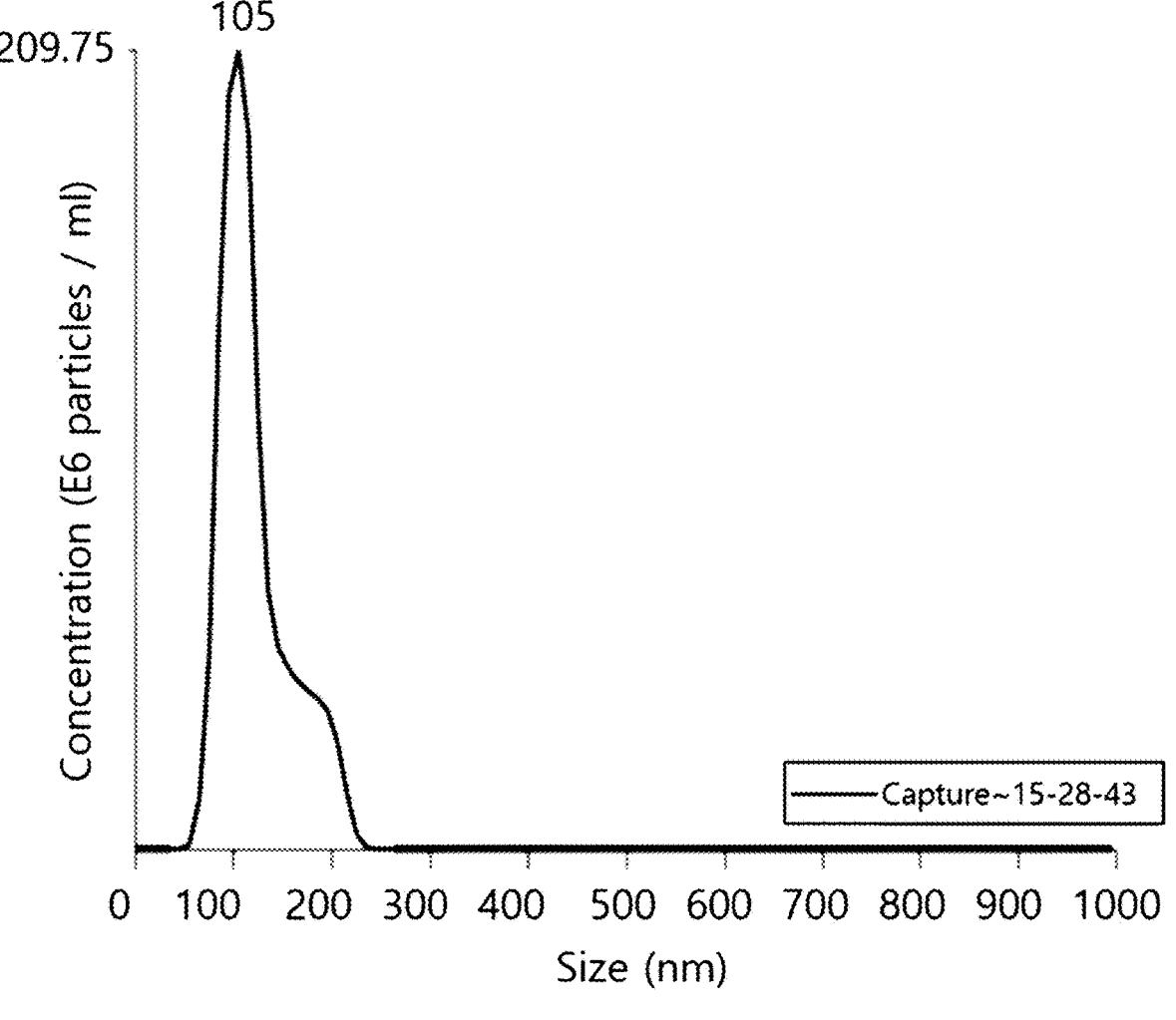
FIG. 4*a* is a graph showing the mean size and distribution of exosomes ((BxC-G63e) isolated from induced pluripotent stem cell-derived mesenchymal stem cells (BxC) pretreated with exendin-4.
Figure 4B:
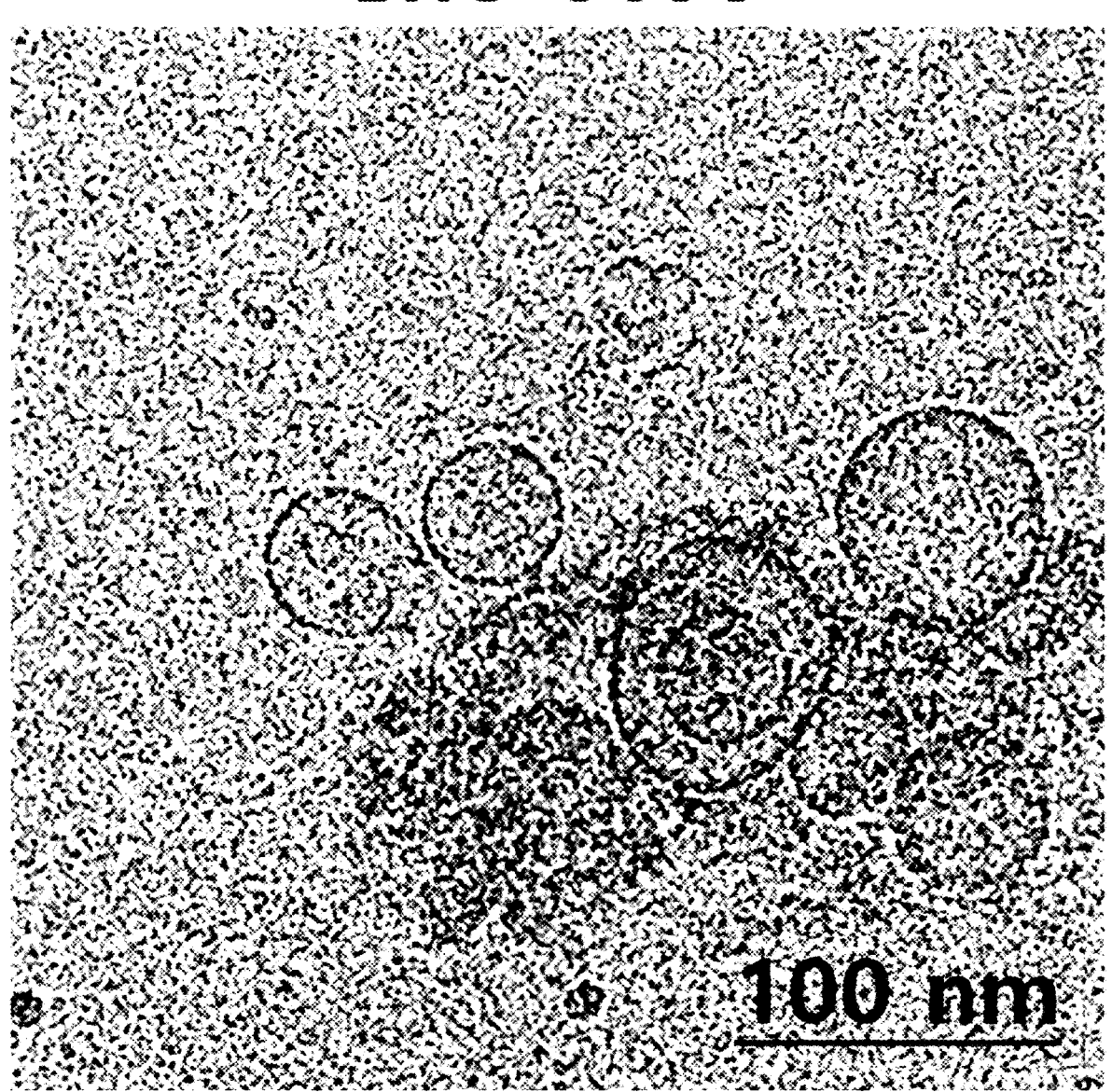
FIG. 4*b* is an electron microscopic image of exosomes (BxC-G63e) isolated from induced pluripotent stem cell-derived mesenchymal stem cells (BxC) pretreated with exendin-4.

As shown in FIGS. 2a and 2b, the BxC-derived exosomes (BxC-e) of the present disclosure exhibited an excellent inhibitory effect on lipogenesis.

Example 2: Isolation of Exosomes from Induced Pluripotent Stem Cell-Derived Mesenchymal Stem Cells According to Treatment with Pretreatment Material 2-1. Exosomes (BxC-V37e) Isolated from Induced Pluripo-tent Stem Cell-Derived Mesenchymal Stem Cells According to Treatment with Lanifibranor The induced pluripotent stem cell (iPSC)-derived mesen-chymal stem cells (BxC) prepared in Preparation Example were cultured for 24 hours in a culture medium [high glucose DMEM (Gibco, Cat no. 11995-065); 10% fetal bovine Serum (HyClone), 1% MEM Non-Essential Amino Acids Solution (100×) (Gibco, Cat no. 11140-050)] supple-mented with 10 μM LANIFIBRANOR.

After completion of culturing, the LANIFIBRANOR-pretreated BxC was washed and incubated for an additional 72 hours in a culture medium supplemented with exosome-depleted, 10% fetal bovine serum (FBS). The use of exosome-depleted FBS is to prevent the incorporation of FBS-derived exosomes other than the exosomes secreted from the mesenchymal stem cells of the present disclosure because general fetal bovine serum per se contains a large amount of exosomes.

After 72 hours of incubation, the culture of BxC treated with the pretreatment material was collected and centrifuged at 300×g for 10 minutes to remove the cells and cell debris. The supernatant thus formed was filtered through a 0.22-μm filter, followed by centrifugation at 10,000×g and 4° C. for 70 minutes in a high-speed centrifuge. The resulting supernatant was subjected to ultracentrifugation at 100,000×g and 4° C. for 90 minutes. Exosomes were obtained as a pellet which was then diluted in PBS (phosphate buffered saline) for use in subsequence experiments.

2-2. Exosomes (BxC-G63e) Isolated from Induced Pluripotent Stem Cell-Derived Mesenchymal Stem Cells Treated with Exendin-4

Exosomes were isolated from in the same manner as in Example 2-1, with the exception that the cells were treated with Exendin-4 (20 nM) instead of Lanifibranor.

Experimental Example 3: Characterization of Exosomes Isolated from Induced Pluripotent Stem Cell-Derived Mesenchymal Stem Cells Treated with Pretreatment Material Exosomes (BxC-V37e and BxC-G63e) isolated in Example 2 were each examined for size distribution by using nanoparticle tracking assay (NanoSight NS300, Malvern) and for morphology by using an electron microscope.

As shown in FIGS. 3a to 4b, the exosomes isolated from BxC treated with IVA337 (FIGS. 3a and 3b) and with exendin-4 (FIGS. 4a and 4b) were both observed to retain the traits of exosomes themselves.

Experimental Example 4: Assay for Therapeutic Activity of Exosomes (BxC-V37e) Isolated from LANIFIBRANOR-Treated, Induced Pluripotent Stem Cell-Derived Mesenchymal Stem Cells for Non-Alcoholic Steatohepatitis The following experiments were conducted with exosomes isolated in Example 1 (BxC-e) and Example 2-1 (BxC-V37e).

4-1. Steatosis Induction

Materials and Reagents

A purchase was made of DMEM (Dulbecco's modified Eagle's medium) from Hyclone (Pittsburgh, PA, USA) and of FBS (fetal bovine serum) from Gibco (Grand Island, NY, USA). Fatty acid-free bovine serum albumin (BSA), palmitate, and oleate were purchased from Sigma (St. Louis, MO, USA).

Human Hepatocyte (HepG2) Culturing

Human hepatocytes (HepG2, ATTC) were cultured at 37° C. in DMEM supplemented with 10% FBS (Gibco) and 1% penicillin-streptomycin under a 5% $CO_2$ condition. The cultured cells were seeded at a predetermined concentration ($5 \times 10^5$ cells/1000 μl/well) into 6-well plates and incubated until the cells became completely adherent to the wells with the intact morphology thereof and reached 95% confluency before use.

Free Fatty Acid (FFA) Preparation (1) Preparation of 1 M Palmitate and 1 M Oleate Storage Solution The solution was prepared at 60° C. using 70% ethanol and deionized distilled water ($ddH_2O$) as solvents, followed by filtration through a 0.2-μm filter and sterilization.

(2) Preparation of 1% (w/v) BSA Solution Containing No Free Fatty Acid

The solution was prepared using deionized distilled water as a solvent, followed by sterilization and refrigeration at 4° C.

(3) Preparation of Mixed Fatty Acid Having 100 mM of Palmitate and Oleate

The fatty acid prepared in (1) was diluted to a concentration of 100 mM using the 1% (w/v) BSA solution containing no free fatty acids, prepared in (2), as a solvent. [10 μl of 1 M palmitate prepared in (1)+290 μl of 1% (w/v) BSA (33 mM)] and [10 μl of 1 M oleate prepared in (1)+140 μl of 1% (w/v) BSA (66 mM)] were mixed at a volume ratio of 1:1 in a heat block maintained at 70° C.

(4) Preparation of 1 mM Mixed, Free Fatty Acid (FFA)

With 10 μl of the 100 mM mixed fatty acid prepared in (3) (oleate and palmitate in 1% (w/v) BSA were mixed at a concentration ratio of 2:1), 990 μl of serum-free DMEM supplemented with 1% penicillin-streptomycin was mixed so that the FFA had a final concentration of 1 mM.

(5) Preparation of BSA Control Solution

The BSA prepared in (2) was used as a control solution.

Steatosis Induction

After the medium thereof was discarded, the HepG2 that had reached 95% confluence was washed once with PBS. Then, the 1 mM mixed free fatty acid prepared in (4) was added in an amount of 1 ml/well to the 6-well plates. For a vehicle control, a serum-free medium treated with the same amount of a vehicle was added. All treatments were conducted overnight (16 hours).

4-2. Assay for Therapeutic Activity for Non-Alcoholic Steatohepatitis

The HepG2 cells treated for 16 hours were washed once with PBS and then incubated with 100 μg of each of BxC-e and BxC-V37e, isolated in Examples 1 and 2, respectively, in a 1 ml serum-free medium for 24 hours before the following experiments.

① Inhibitory Effect on Lipogenesis

To each well of the 6-well plates, Trizol solution was added in an amount of 1 ml to lyse the human hepatocytes. The cell lysate was mixed with 200 μl of chloroform and vortexed, followed by centrifugation at 4° C. and 12,000 rpm for 15 minutes. The supernatant thus formed was transferred to a new tube and mixed with 500 μl of isopropanol. The tube was turned upside down 50 times, left on ice for 5 min, and then centrifuged at 12,000 rpm and 4° C. for 10 minutes. The supernatant was discarded and the pellet was added with 1 ml of 70% ethanol and briefly spun down at 12,000 rpm and 4° C. for 5 minutes. After removal of ethanol, the RNA pellet in the tube was dried at room temperature to invisibility. Then, the RNA pellet was dissolved in nuclease-free water. Concentrations of the RNA samples were measured using Nanodrop at 260 nm/280 nm. From the RNA sample, cDNA was synthesized using an RT premix.

On the synthesized cDNA, real time-polymerase chain reaction (PCR) was performed with synthesized primers (COSMOgenetech) (see Table 1 below) to monitor mRNA expression of FABP4.

TABLE 1

| Gene | Primer | Sequence (5'-3') |
|------|--------|------------------|
| FABP4 | F | GCATGGCCAAACCTAACATG (SEQ ID NO: 1) |
| | R | CCTGGCCCAGTATGAAGGAA (SEQ ID NO: 2) |

Figure 5:
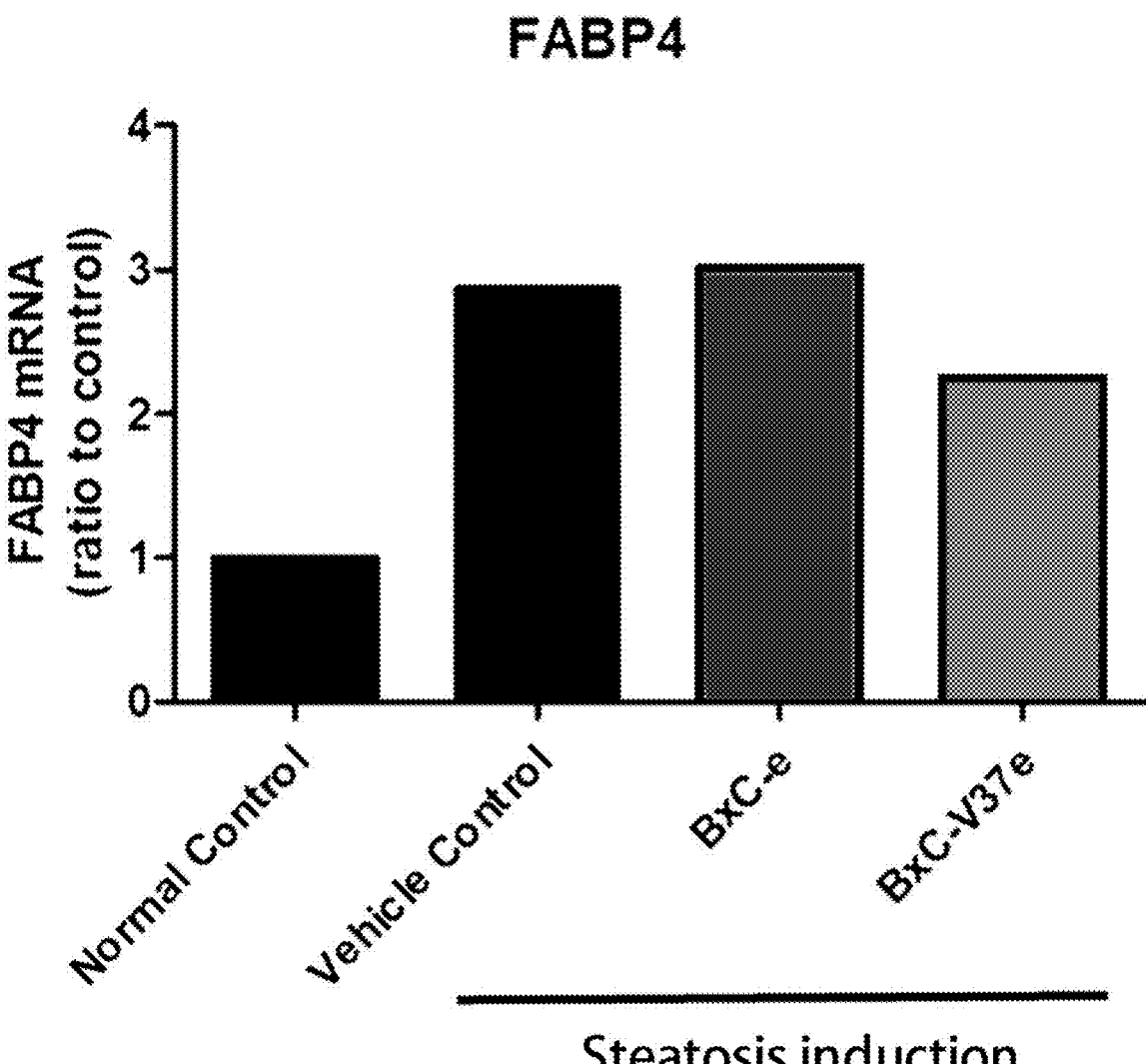
FIG. 5 is a graph showing inhibitory effects of exosomes (BxC-e) isolated from induced pluripotent stem cell-derived mesenchymal stem cells (BxC) and exosomes (BxC-V37e) isolated from induced pluripotent stem cell-derived mesenchymal stem cells (BxC) pretreated with LANIFIBRANOR on lipogenesis in steatosis-induced hepatocytes.

As shown in FIG. 5, a lower expression level of FABP4 gene, which is involved in lipogenesis, was detected in the group where the human hepatocytes had undergone steatosis induction and then treatment with BxC-V37e than in the non-treated groups. These data imply that BxC-V37e has highly inhibitory activity against lipogenesis.

② Inhibitory Effect on Inflammation mRNA expression changes of TNF-α and MCP1 were examined in a similar manner to that of Example 4-①. The primers used are listed in Table 2, below.

TABLE 2

| Gene | Primer | Sequence (5'-3') |
|------|--------|------------------|
| TNF-α | F | GAGCTGAACAATAGGCTGTTCCCA (SEQ ID NO: 3) |
| | R | AGAGGCTCAGCAATGAGTGACAGT (SEQ ID NO: 4) |
| MCP1 | F | TCTGTGCCTGCTGCTCATAG (SEQ ID NO: 5) |
| | R | GGGCATTGATTGCATCTGGC (SEQ ID NO: 6) |

Figure 6A:
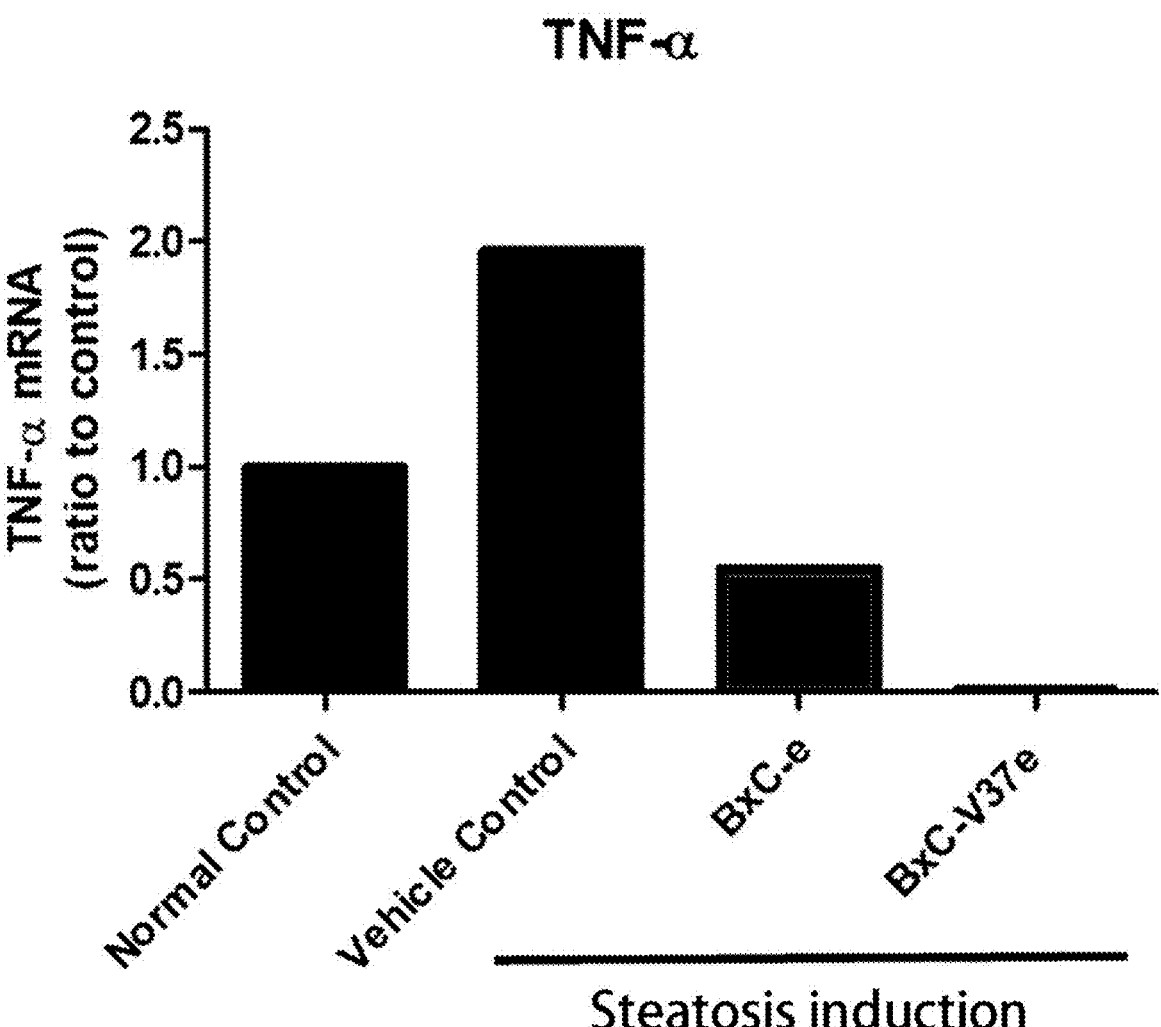
FIGS. 6*a* and 6*b* are graphs showing inhibitory effects of exosomes (BxC-e) isolated from induced pluripotent stem cell-derived mesenchymal stem cells (BxC) and exosomes (BxC-V37e) isolated from induced pluripotent stem cell-derived mesenchymal stem cells (BxC) pretreated with LANIFIBRANOR on inflammation in steatosis-induced hepatocytes.
Figure 6B:
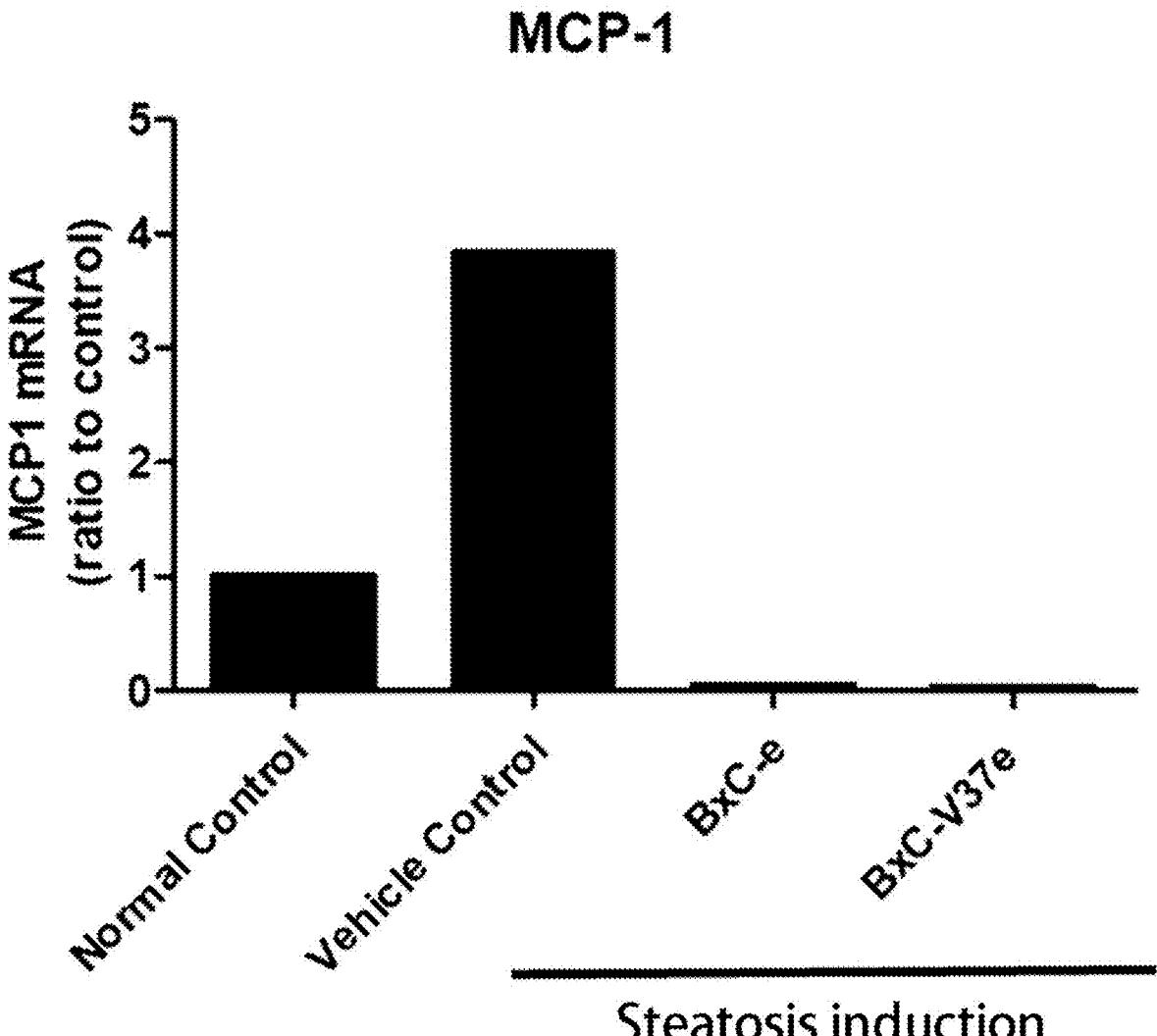

As can be seen in FIGS. 6a and 6b, the group where the human hepatocytes had undergone steatosis induction and treatment with BxC-V37e was observed to significantly decrease in expression levels of TNF-α and MCP-1, which are expressed upon inflammation induction, compared to the non-treated groups, demonstrating the excellent anti-inflammatory activity of BxC-V37e in a lipogenesis-induced inflammatory condition.

③ Inhibitory Effect on ER Stress

A mRNA expression change of CHOP was examined in a similar manner to that of Example 4-①. The primers used are listed in Table 3, below.

TABLE 3

| Gene | Primer | Sequence (5'-3') |
|------|--------|------------------|
| CHOP | F | AGGGAGAACCAGGAAACGGAAACA (SEQ ID NO: 7) |
| | R | TCCTGCTTGAGCCGTTCATTCTCT (SEQ ID NO: 8) |

Figure 7:
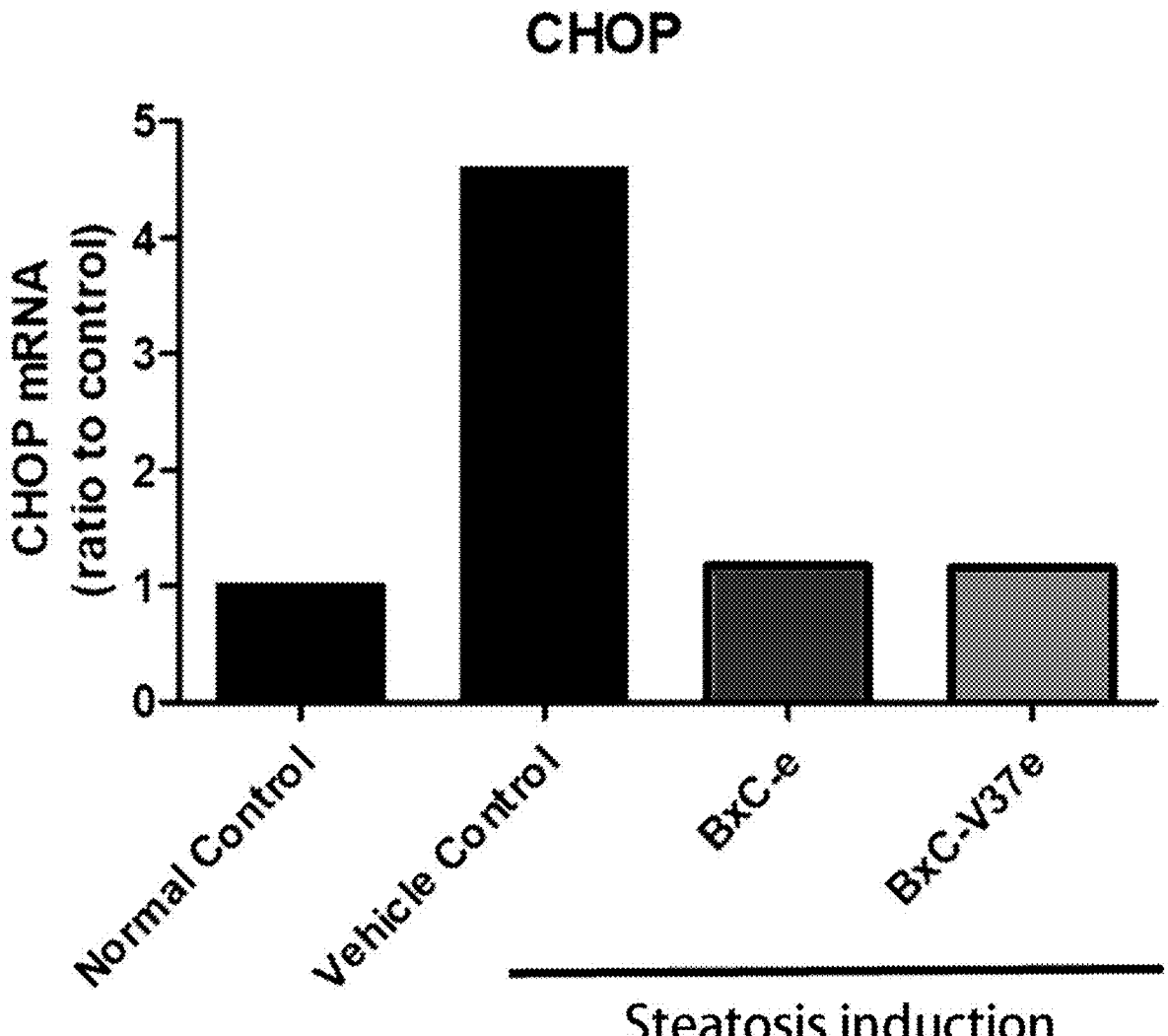
FIG. 7 is a graph showing inhibitory effects of exosomes (BxC-e) isolated from induced pluripotent stem cell-derived mesenchymal stem cells (BxC) and exosomes (BxC-V37e) isolated from induced pluripotent stem cell-derived mesenchymal stem cells (BxC) pretreated with LANIFIBRANOR on ER stress in steatosis-induced hepatocytes.

As understood from the data of FIG. 7, the expression level of CHOP gene, which is responsible for ER stress, was significantly decreased in the group where the human hepatocytes had undergone steatosis induction and treatment with BxC-V37e, compared to the non-treated groups, implying that BxC-V37e has excellent inhibitory activity against lipogenesis-induced ER stress.

Experimental Example 5: Assay for Therapeutic Activity of Exosomes (BxC-G63e) Isolated from Exendin-4-Treated, Induced Pluripotent Stem Cell-Derived Mesenchymal Stem Cells for Non-Alcoholic Steatohepatitis The following experiments were conducted with exendin-4 and exosomes isolated in Example 2-2 (BxC-G63e).

5-1. Steatosis Induction

Materials and Reagents

A purchase was made of DMEM (Dulbecco's modified Eagle's medium) from Hyclone (Pittsburgh, PA, USA) and of FBS (fetal bovine serum) from Gibco (Grand Island, NY, USA). Fatty acid-free bovine serum albumin (BSA), palmitate, and oleate were purchased from Sigma (St. Louis, MO, USA).

Human Hepatocyte (HepG2) Culturing

Human hepatocytes (HepG2, ATTC) were cultured at 37° C. in DMEM supplemented with 10% FBS (Gibco) and 1% penicillin-streptomycin under a 5% $CO_2$ condition. The cultured cells were seeded at a predetermined concentration ($5 \times 10^5$ cells/1000 μl/well) into 6-well plates and incubated until the cells became completely adherent to the wells with the intact morphology thereof and reached 95% confluency before use.

Free Fatty Acid (FFA) Preparation (1) Preparation of 1 M Palmitate and 1 M Oleate Storage Solution The solution was prepared at 60° C. using 70% ethanol and deionized distilled water ($ddH_2O$) as solvents, followed by filtration through a 0.2-μm filter and sterilization.

(2) Preparation of 1% (w/v) BSA Solution Containing No Free Fatty Acid

The solution was prepared using deionized distilled water as a solvent, followed by sterilization and refrigeration at 4° C.

(3) Preparation of Mixed Fatty Acid Having 100 mM of Palmitate and Oleate

The fatty acid prepared in (1) was diluted to a concentration of 100 mM using the 1% (w/v) BSA solution containing no free fatty acids, prepared in (2), as a solvent. [10 μl of 1 M palmitate prepared in (1)+290 μl of 1% (w/v) BSA (33 mM)] and [10 μl of 1 M oleate prepared in (1)+140 μl of 1% (w/v) BSA (66 mM)] were mixed at a volume ratio of 1:1 in a heat block maintained at 70° C.

(4) Preparation of 1 mM Mixed, Free Fatty Acid (FFA)

With 10 μl of the 100 mM mixed fatty acid prepared in (3) (oleate and palmitate in 1% (w/v) BSA were mixed at a concentration ratio of 2:1), 990 μl of serum-free DMEM supplemented with 1% penicillin-streptomycin was mixed so that the FFA had a final concentration of 1 mM.

(5) Preparation of BSA Control Solution

The 1% (w/v) BSA prepared in (2) was used as a control solution.

Steatosis Induction

After the medium thereof was discarded, the HepG2 that had reached 95% confluence was washed once with PBS. Then, the 1 mM mixed free fatty acid prepared in (4) was added in an amount of 1 ml/well to the 6-well plates. For a vehicle control, a serum-free medium treated with the same amount of a vehicle was added. All treatments were conducted overnight (16 hours).

5-2. Assay for Therapeutic Activity for Non-Alcoholic Steatohepatitis

The HepG2 cells treated for 16 hours were washed once with PBS and then incubated with 100 μg of each of 20 nM exendin-4 and BxC-G63e isolated in Example 2 in a 1 ml serum-free medium for 24 hours before the following experiments.

① Inhibitory Effect on Lipogenesis

To each well of the 6-well plates, Trizol solution was added in an amount of 1 ml to lyse the human hepatocytes. The cell lysate was mixed with 200 μl of chloroform and vortexed, followed by centrifugation at 4° C. and 12,000 rpm for 15 minutes. The supernatant thus formed was transferred to a new tube and mixed with 500 μl of isopropanol. The tube was turned upside down 50 times, left on ice for 5 min, and then centrifuged at 12,000 rpm and 4° C. for 10 minutes. The supernatant was discarded and the pellet was added with 1 ml of 70% ethanol and briefly spun down at 12,000 rpm and 4° C. for 5 minutes. After removal of ethanol, the RNA pellet in the tube was dried at room temperature to invisibility. Then, the RNA pellet was dissolved in nuclease-free water. Concentrations of the RNA samples were measured using Nanodrop at 260 nm/280 nm. From the RNA sample, cDNA was synthesized using an RT premix.

On the synthesized cDNA, real time-polymerase chain reaction (PCR) was performed with synthesized primers (COSMOgenetech) (see Table 4 below) to monitor mRNA expression of FABP4, ACC1, and SREBP1.

TABLE 4

| Gene | Primer | Sequence (5'-3') |
|---|---|---|
| FABP4 | F | GCATGGCCAAACCTAACATG (SEQ ID NO: 1) |
| | R | CCTGGCCCAGTATGAAGGAA (SEQ ID NO: 2) |
| ACC1 | F | GCTCCTTGTCACCTGCTTCT (SEQ ID NO: 9) |
| | R | CAAGGCCAAGCCATCCTGTA (SEQ ID NO: 10) |
| SREBP1 | F | GGAGGGGTAGGGGCCAACGC (SEQ ID NO: 11) |
| | R | CATGTCTTCGAAAGTGCAAT (SEQ ID NO: 12) |

Figure 8A:
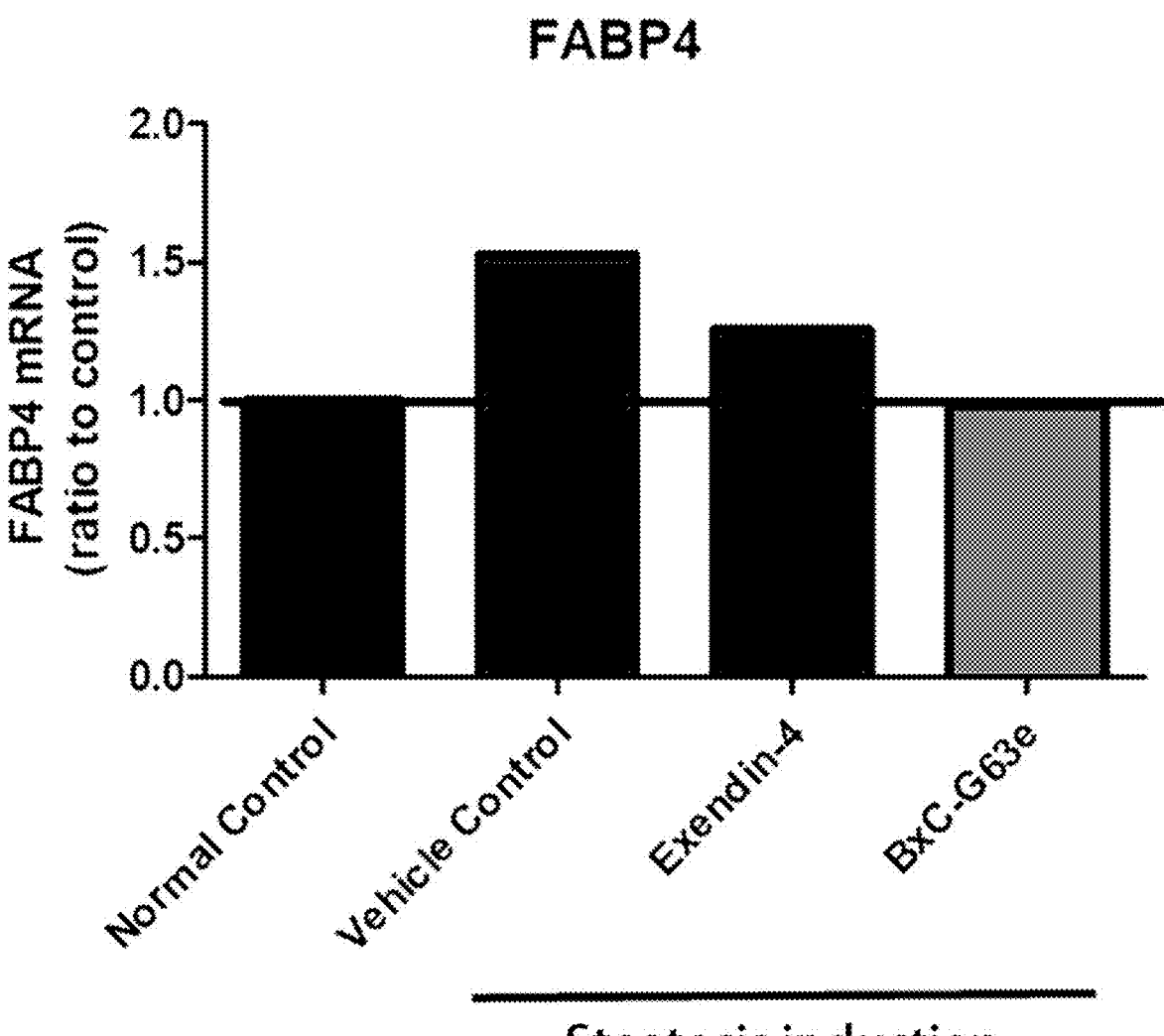
FIGS. 8*a*, 8*b* and 8*c* are graphs showing inhibitory effects of exendin-4 and exosomes (BxC-G63e) isolated from induced pluripotent stem cell-derived mesenchymal stem cells (BxC) pretreated with exendin-4 on lipogenesis in steatosis-induced hepatocytes.
Figure 8B:
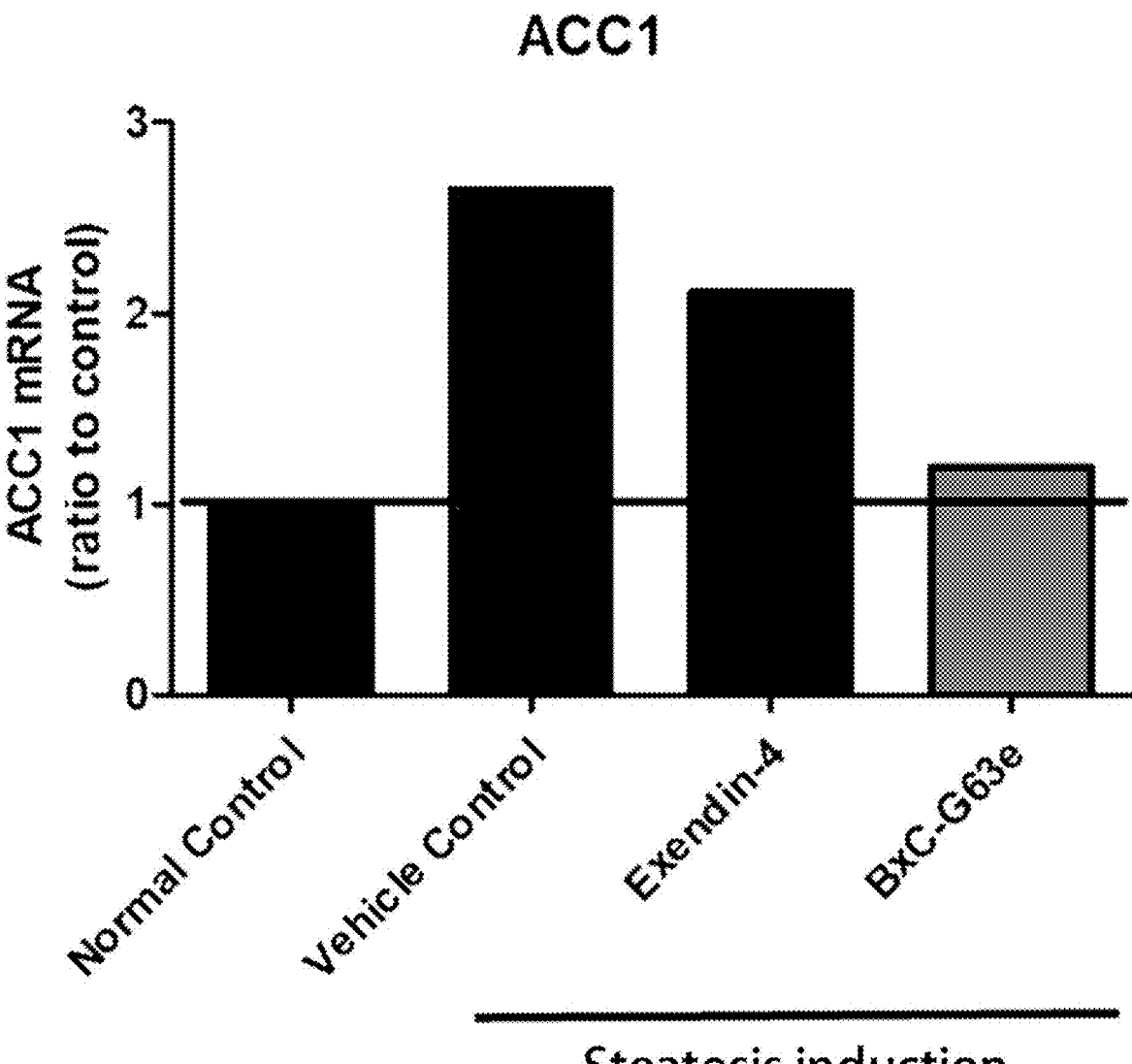
Figure 8C:
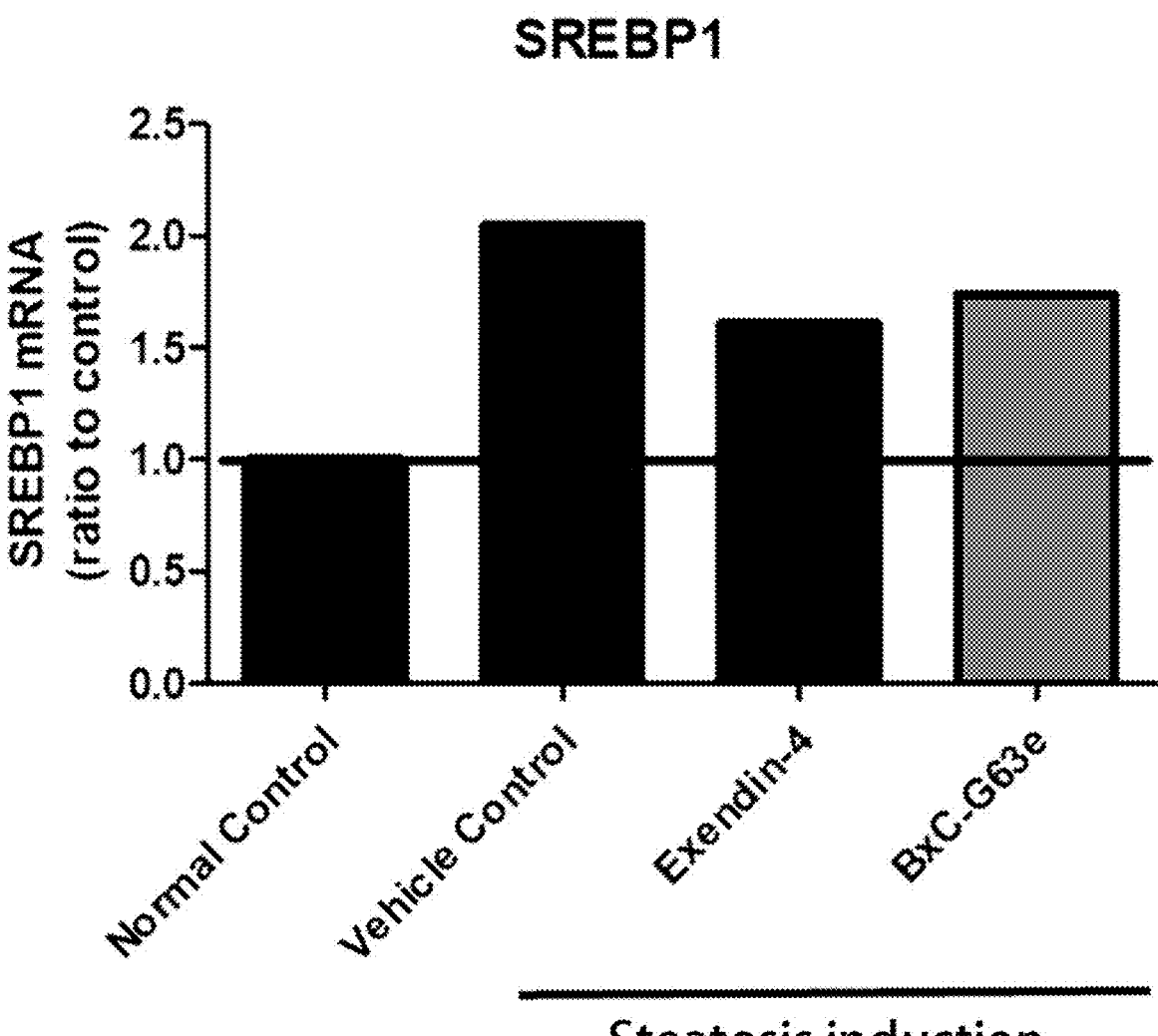

As shown in FIGS. 8a to 8c, lower expression levels of FABP4, ACC1, and SREBP1 gene, which are involved in lipogenesis, were detected in the groups where the human hepatocytes had undergone steatosis induction and then treatment with BxC-G63e than in the non-treated groups. These data imply that BxC-G63e has highly inhibitory activity against lipogenesis.

② Inhibitory Effect on Inflammation mRNA expression changes of TNF-α and IL-10 were examined in a similar manner to that of Example 5-①. The primers used are listed in Table 5, below.

TABLE 5

| Gene | Primer | Sequence (5'-3') |
|---|---|---|
| TNF-α | F | GAGCTGAACAATAGGCTGTTCCCA (SEQ ID NO: 3) |
| | R | AGAGGCTCAGCAATGAGTGACAGT (SEQ ID NO: 4) |

TABLE 5-continued

| Gene | Primer | Sequence (5'-3') |
|---|---|---|
| IL-10 | F | TGAAAACAAGAGCAAGGCCG (SEQ ID NO: 13) |
| | R | GCCACCCTGATGTCTCAGTT (SEQ ID NO: 14) |

Figure 9A:
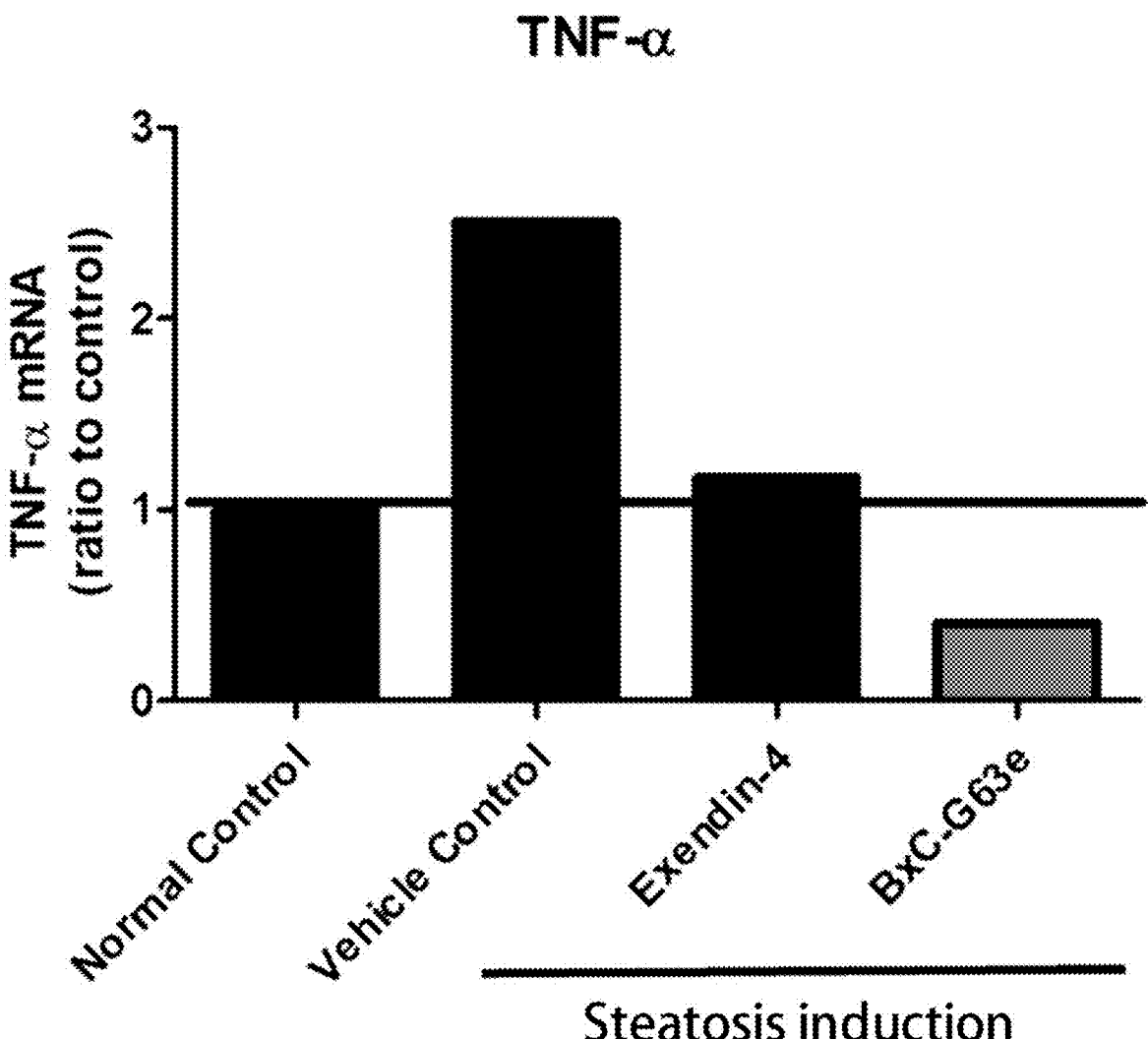
FIGS. 9*a* and 9*b* are graphs showing inhibitory effects of exendin-4 and exosomes (BxC-G63e) isolated from induced pluripotent stem cell-derived mesenchymal stem cells (BxC) pretreated with exendin-4 on inflammation in steatosis-induced hepatocytes.
Figure 9B:
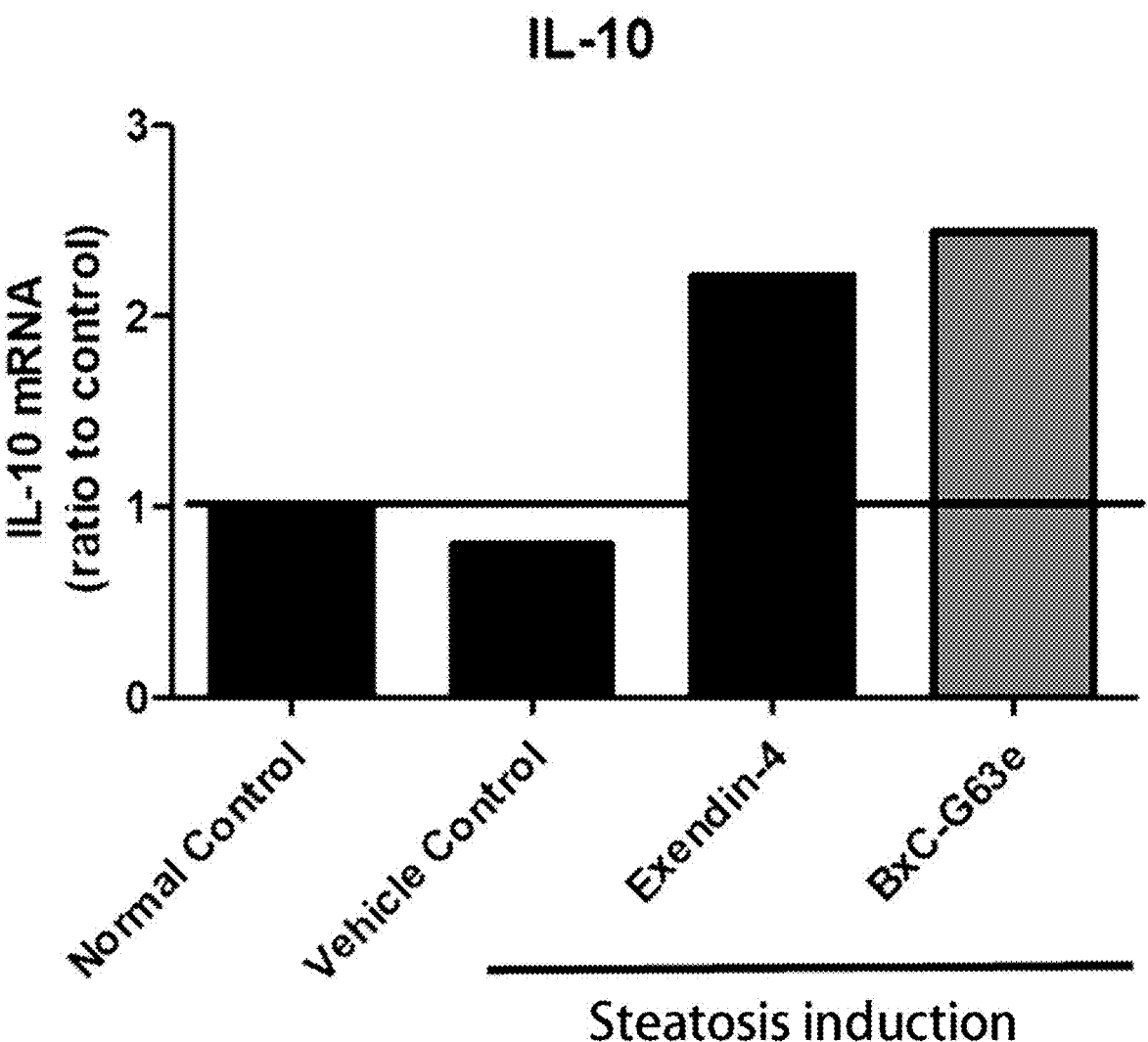

As can be seen in FIGS. 9a and 9b, the groups where the human hepatocytes had undergone steatosis induction and treatment with BxC-G63e were observed to significantly decrease in expression level of TNF-α, which is a pro-inflammatory factor, and significantly increased in expression level of IL-10, which is an anti-inflammatory factor, compared to the non-treated groups, demonstrating the excellent anti-inflammatory activity of BxC-G63e in a lipogenesis-induced inflammatory condition.

③ Inhibitory Effect on ER Stress

Figure 10:
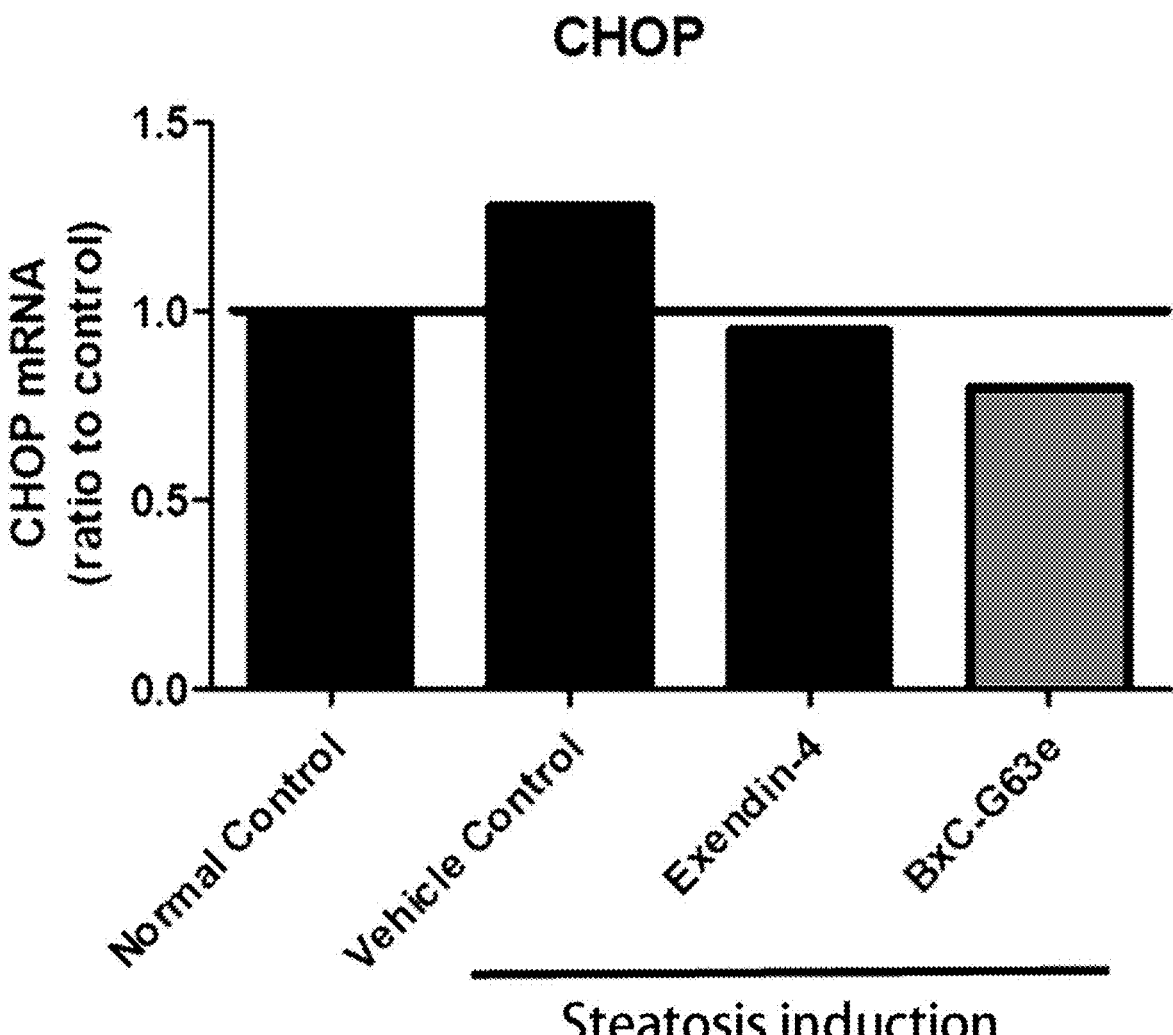
FIG. 10 is a graph showing inhibitory effects of exendin-4 and exosomes (BxC-G63e) isolated from induced pluripotent stem cell-derived mesenchymal stem cells (BxC) pretreated with exendin-4 on ER stress in steatosis-induced hepatocytes.
Figure 11A:
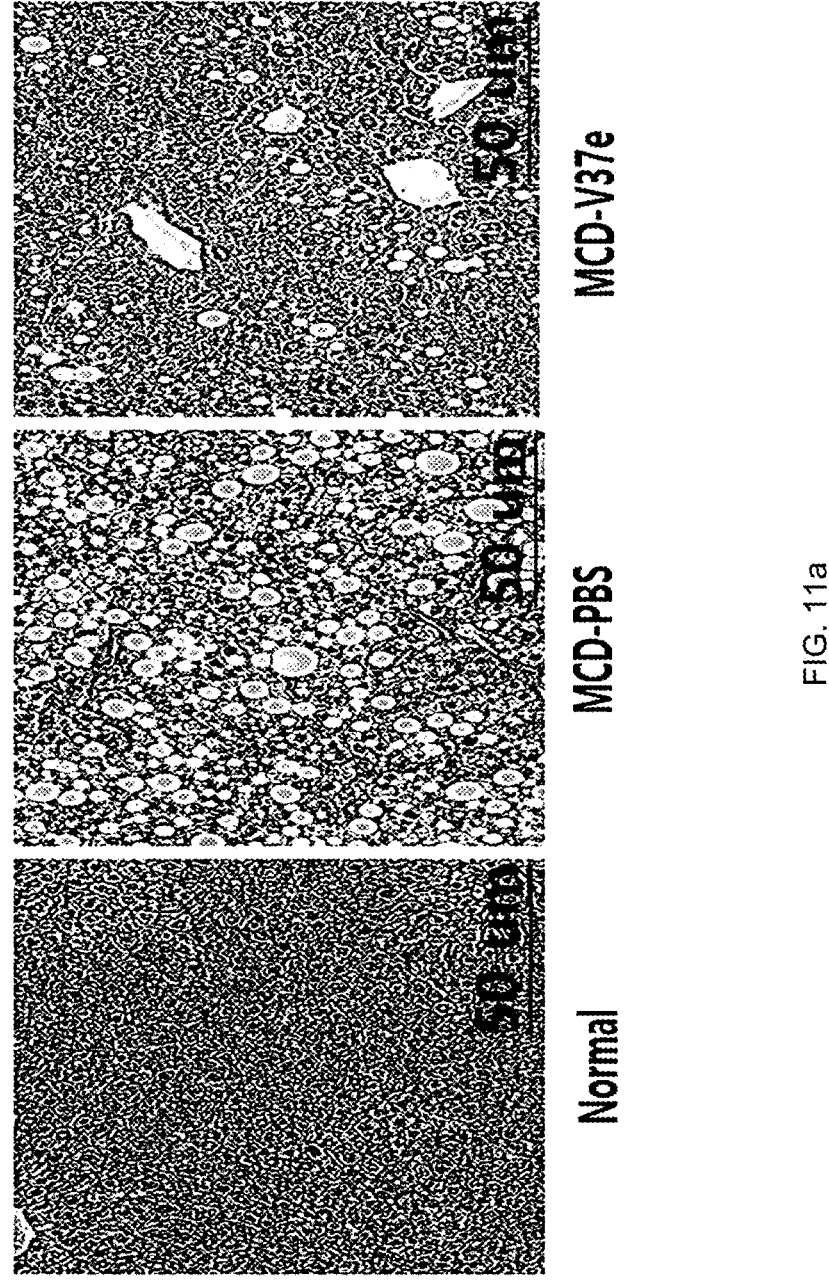
FIG. 11*a* shows microphotographic images of the non-treated normal group (Normal), the PBS-treated control (MCD-PBS), and the BxC-V37e-treated group (MCD-V37e) of hepatocytes from steatosis-induced mice after hematoxylin & eosin (H&E) staining.
Figure 11B:
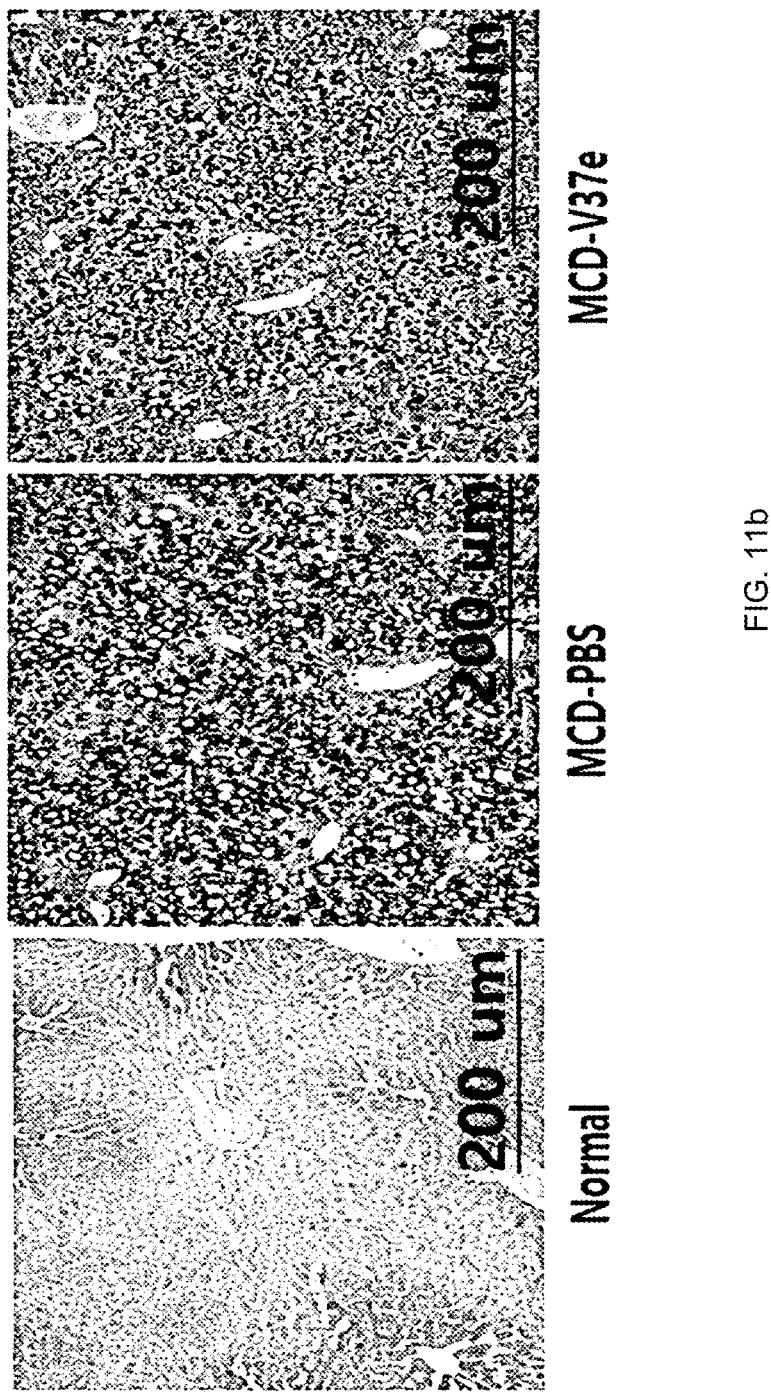
FIG. 11*b* shows microphotographic images of the non-treated normal group (Normal), the PBS-treated control (MCD-PBS), and the BxC-V37e-treated group (MCD-V37e) of hepatocytes from steatosis-induced mice after oil red O staining.
Figure 12A:
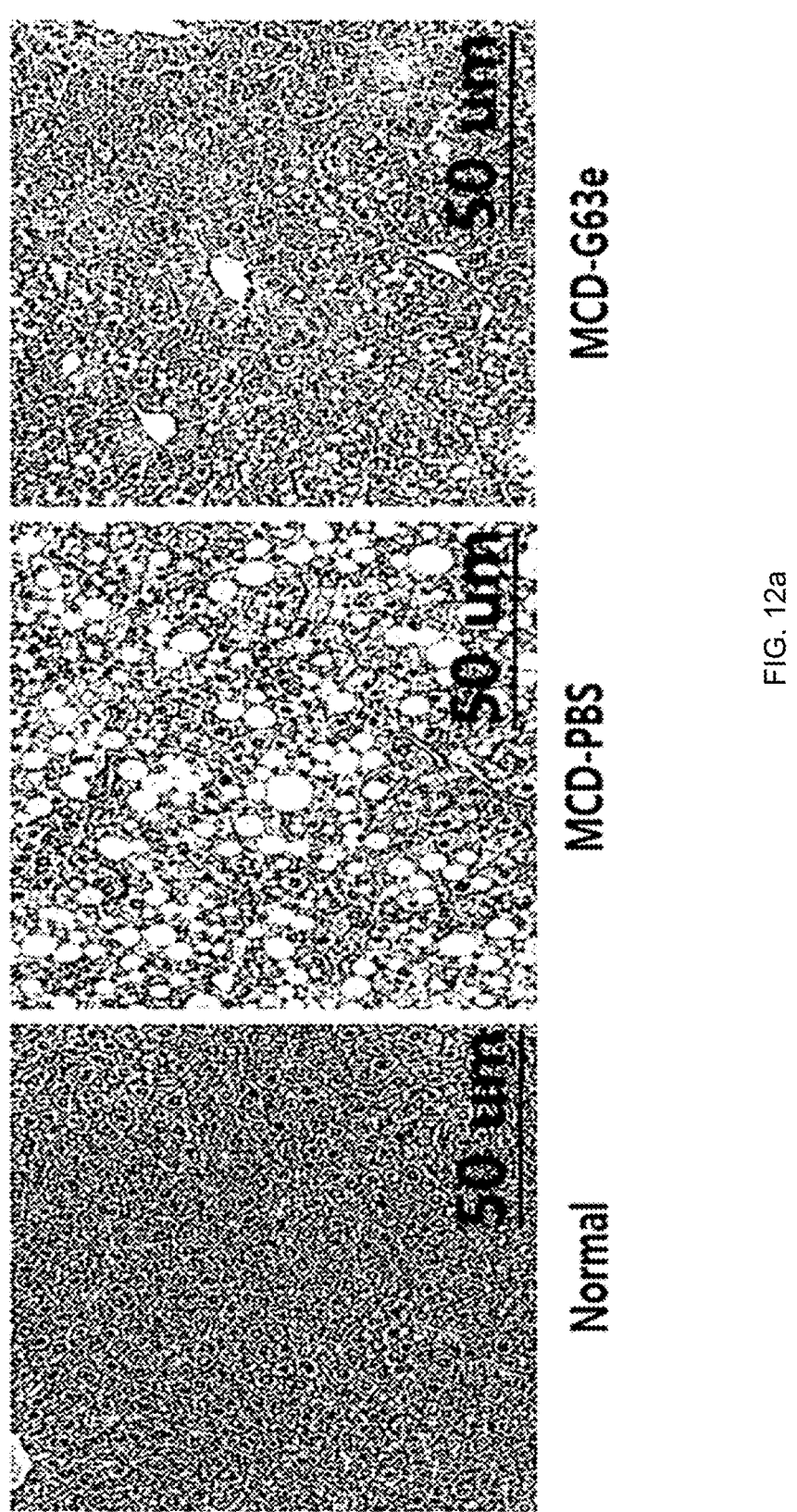
FIG. 12*a* shows microphotographic images of the non-treated normal group (Normal), the PBS-treated control (MCD-PBS), and the BxC-G63e-treated group (MCD-G63e) of hepatocytes from steatosis-induced mice after hematoxylin & eosin (H&E) staining.
Figure 12B:
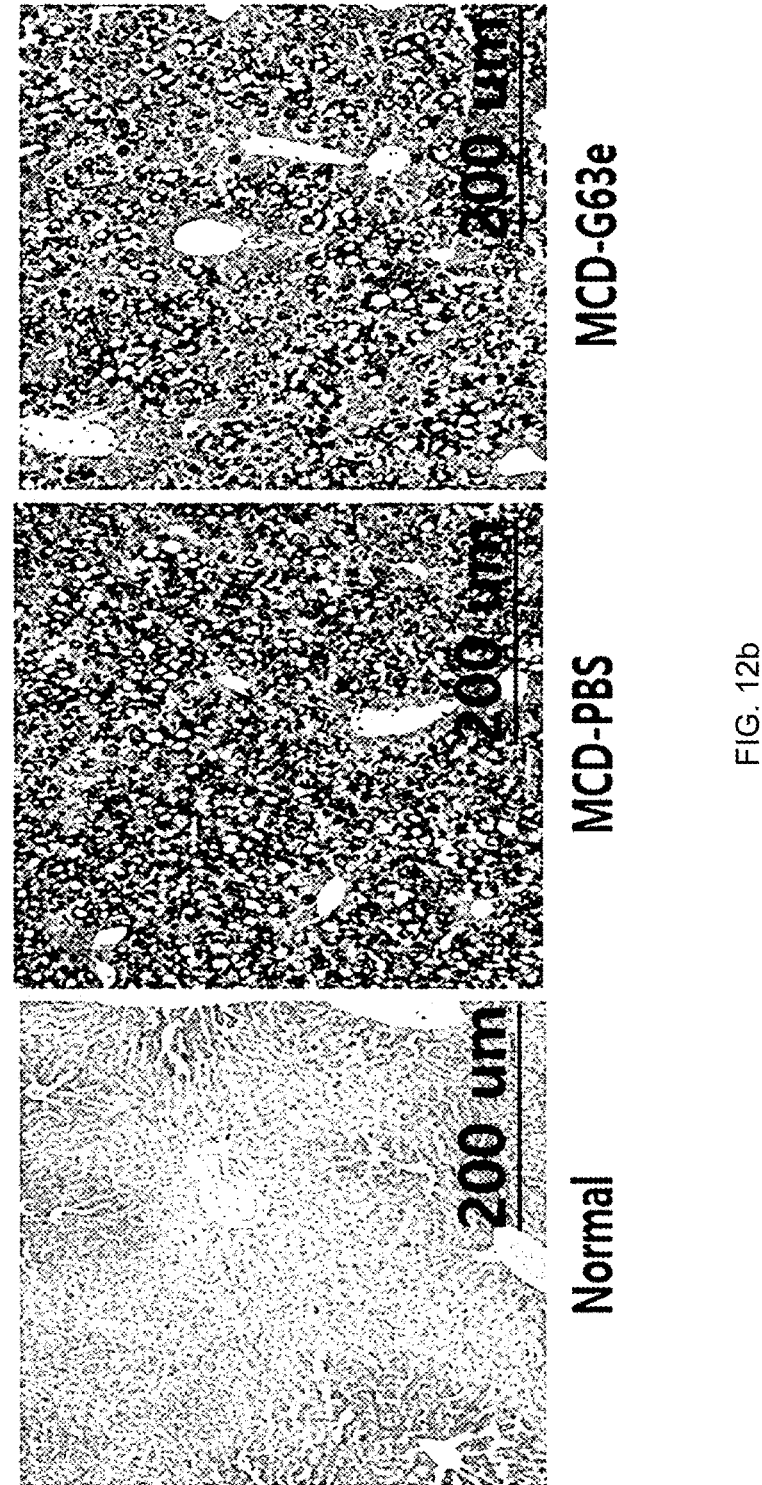
FIG. 12*b* shows microphotographic images of the non-treated normal group, the PBS-treated control (MCD-PBS), and the BxC-G63e-treated group (MCD-G63e) of hepatocytes from steatosis-induced mice after oil red O staining.

A mRNA expression change of CHOP was examined in a similar manner to that of Example 5-①. The primers used are listed in Table 3, above As understood from the data of FIG. 10, the expression level of CHOP gene, which is responsible for ER stress, was significantly decreased in the group the human hepatocytes had undergone steatosis induction and treatment with BxC-G63e, compared to the non-treated groups, implying that BxC-G63e has excellent inhibitory activity against lipogenesis-induced ER stress.

Experimental Example 6: Assay for Therapeutic Activity of BxC-V37e and BxC-G63e for Non-Alcoholic Steatohepatitis in MCD-Diet Mouse Model The following experiments were conducted with the exosomes isolated in Examples 2-1 (BxC-V37e) and 2-2 (BxC-G63e).

6-1. Induction of Steatosis in MCD-Diet Mouse

MCD Diet Mouse Raising Condition

C57BL/6NHsd male mice were raised in the environment which was set for temperature 23±3° C., relative humidity 55±15%, ventilation 10-20 times/hr, lightening 12 hours (light on a.m. 8-light off p.m. 8), and illumination intensity 150-300 Lux. The environment was monitored regularly.

MCD Diet Feeding

The C57BL/6NHsd male mice at 6 weeks of age were allowed to freely approach MCD diet and normal diet for 12 weeks in such a pattern as to feed MCD diet for first 5 days and the normal diet for subsequent 2 days.

Preparation and Administration of Test Substance

BxC-G63e and BxC-V37e were diluted in PBS to prepare respective test substances. The test substance was intravenously injected at a dose of 100 μg/head to 400 μg/head on the basis of the protein therein once a day and three times a week for 4 weeks. The test substance was slowly injected at a speed of 1 mL/min via the tail vein using a syringe with 26-gauge needle after the six-week-old C57BL/6NHsd male mice were restrained in a holder.

6-2. Assay for Therapeutic Activity for Non-Alcoholic Steatohepatitis

The liver was excised from the C57BL/6NHsd male mice injected with the test substance, photographed, and weighed. The right lobe was fixed in 10% neutral buffered formalin while the left lobe was quenched with liquid nitrogen before use in the following experiments.

US 12,594,303 B2

21

① Inhibitory Effect on Lipogenesis
Histopathological Examination

After general tissue processes including trimming, dehydration, paraffin embedding, and sectioning, the fixed liver tissue was prepared into specimens for histopathological examination. The specimens were stained with hematoxylin & eosin (H&E) and oil red O and examined for histopathological change under an optical microscope (Olympus BX53, Japan).
NAS Scoring Microvesicular steatosis, macrovesicular steatosis, and hepatocellular hypertrophy were scored and graded into 0-3 points, based on the percentage of the total area affected on fields of view at 40× to 100× magnifications under a microscope. Inflammation was scored for five foci on the field of view at 100× magnification into 0-3 points, followed by comparison among groups.

As can be seen in FIGS. 11a to 11b and FIGS. 12a and 12b, the groups which had been treated with BxC-G63e or BxC-V37e after induction of steatosis with MCD diet were observed to remarkably decrease in the size and number of lipid droplets, compared to the untreated control.

Figure 13A:
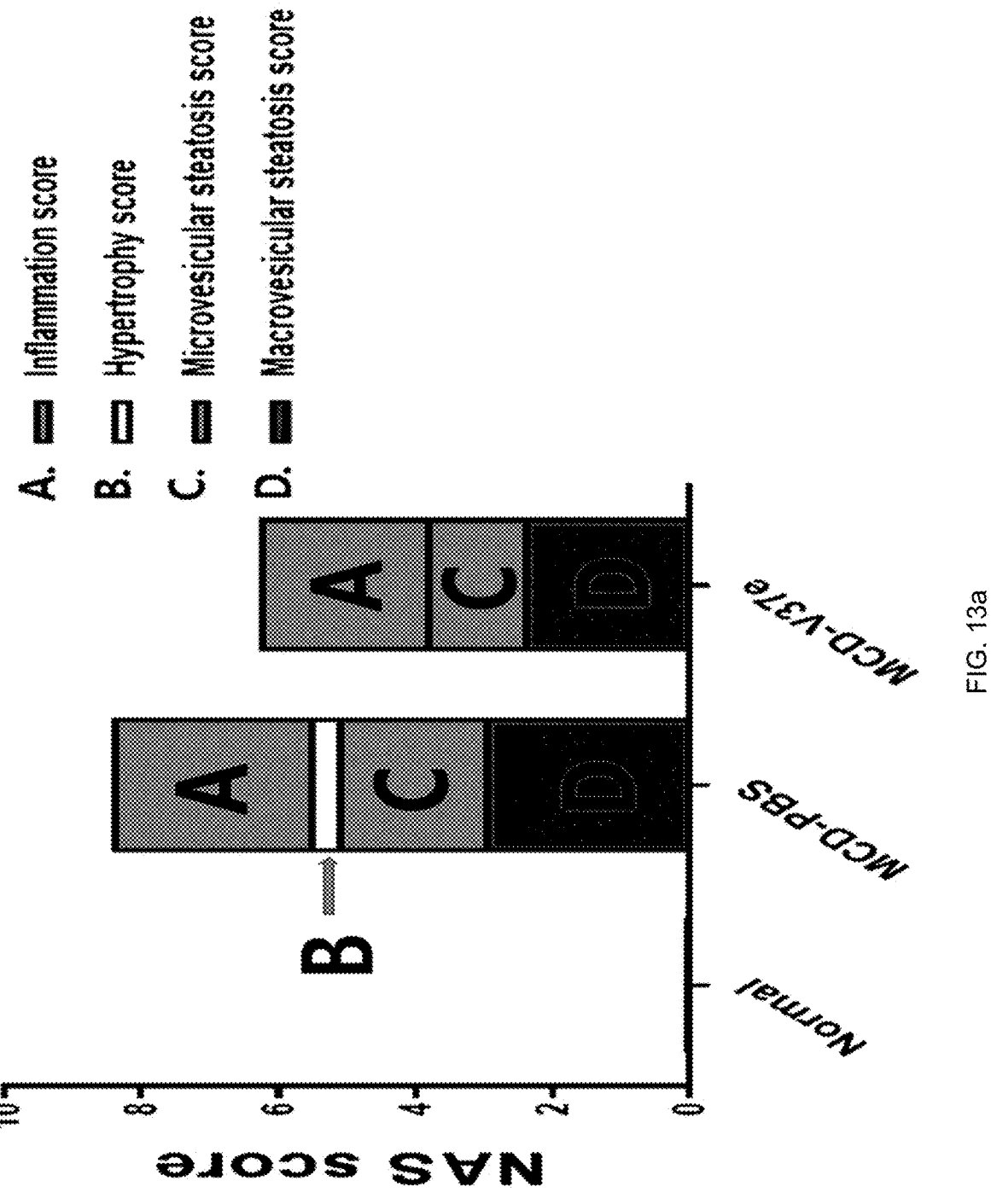
FIG. 13*a* is a graph showing NAS scores of the non-treated normal group (Normal), the PBS-treated control (MCD-PBS), and the BxC-V37e-treated group (MCD-V37e) of hepatocytes from steatosis-induced mice.
Figure 13B:
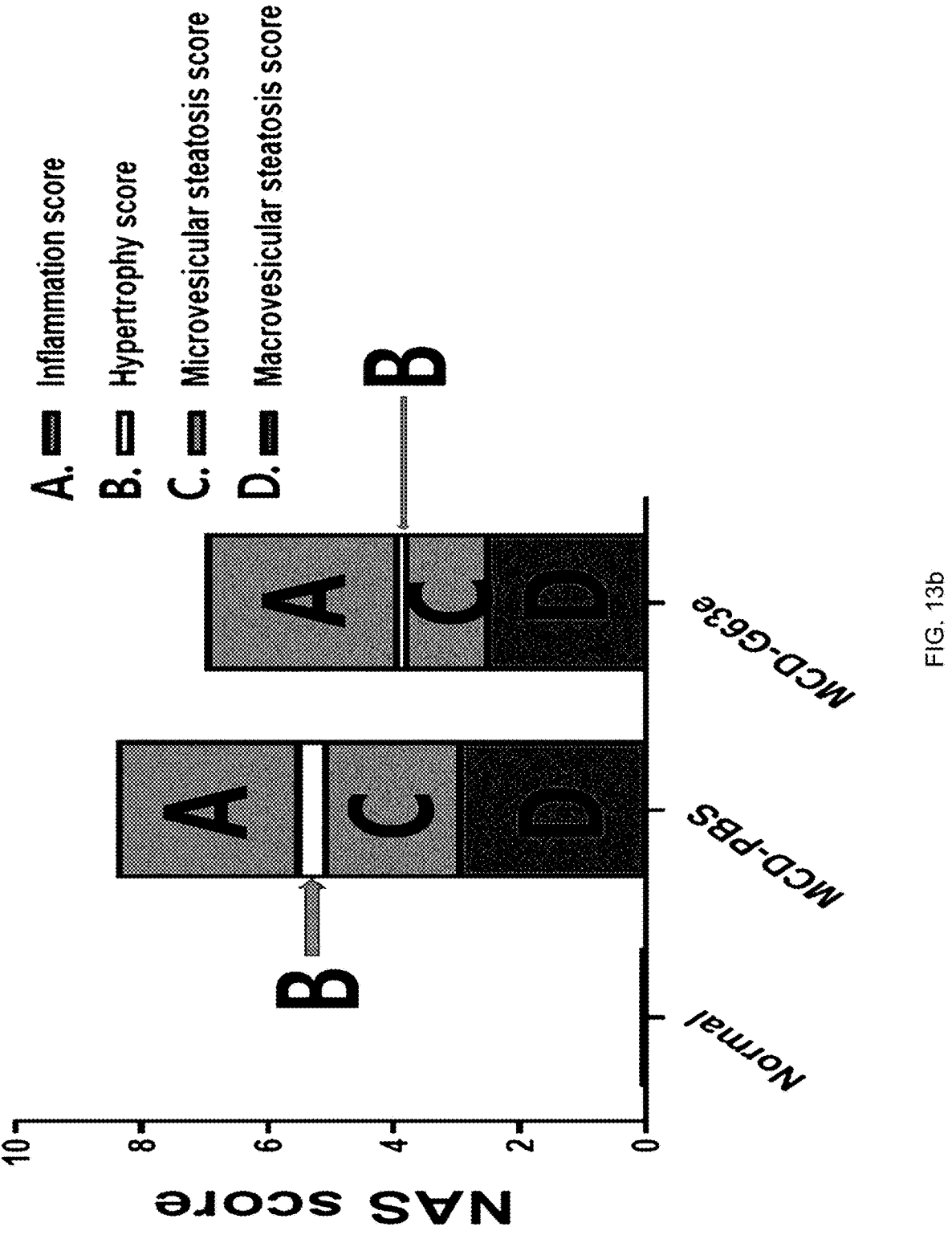
FIG. 13*b* is a graph showing NAS scores of the non-treated normal group, the PBS-treated control (MCD-PBS), and the BxC-G63e-treated group (MCD-G37e) of hepatocytes from steatosis-induced mice.

In addition, as shown in FIG. 13a or 13b, NAS scores for microvesicular steatosis, macrovesicular steatosis, and hepatocellular hypertrophy were all decreased in the treated groups. The data imply the BxC-G63e or BxC-V37e has excellent inhibitory activity against lipogenesis.
② Inhibitory Effect on Inflammation After general tissue processes including trimming, dehydration, paraffin embedding, and sectioning, the fixed liver tissue was prepared into specimens for immunohistochemical staining. The specimens were reacted with an anti-TNF-α antibody as a primary antibody and then with a secondary antibody specific therefor before examination on expression levels of TNF-α protein.

Figure 14A:
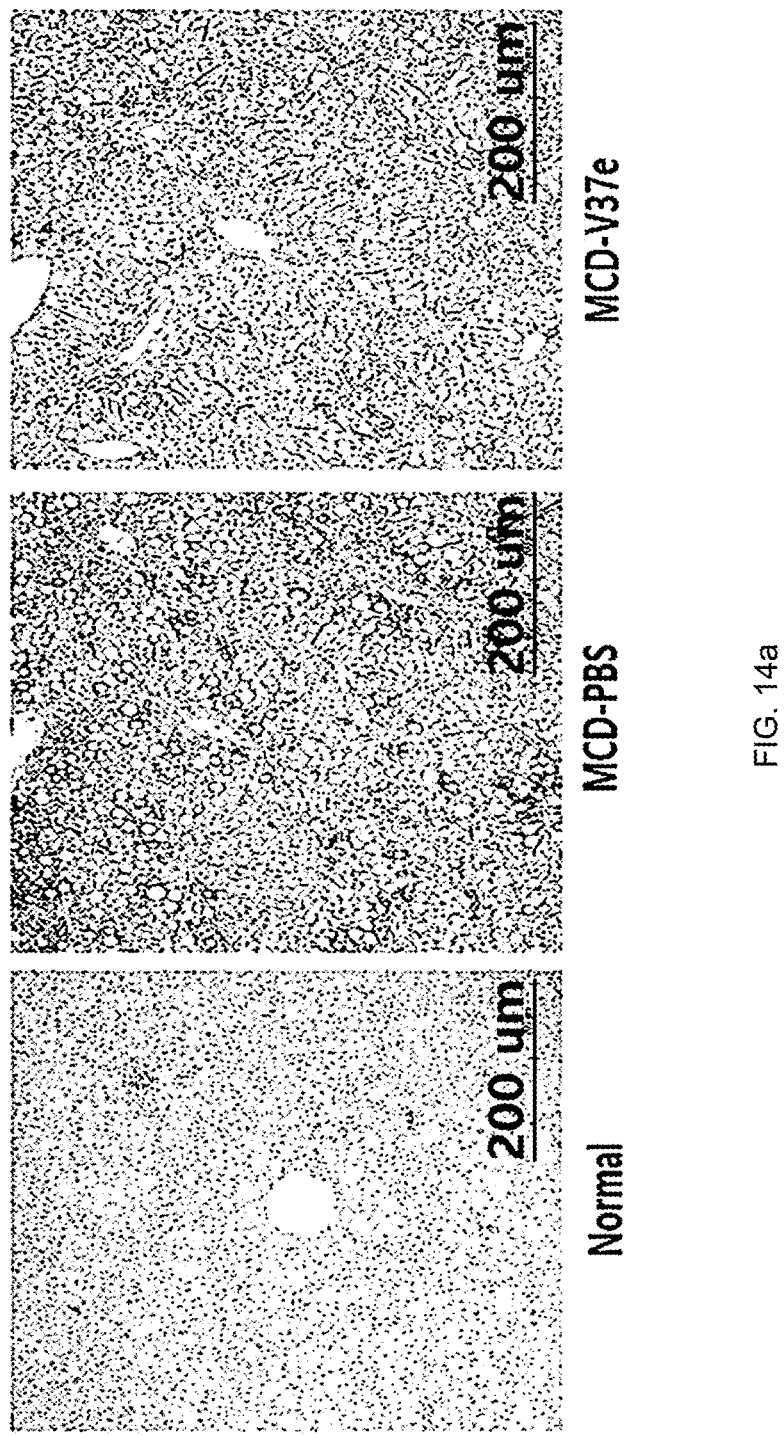
FIG. 14*a* shows microphotographic images of the non-treated normal group (Normal), the PBS-treated control (MCD-PBS), and the BxC-V37e-treated group (MCD-V37e) of hepatocytes from steatosis-induced mice after immunohistochemical staining.
Figure 14B:
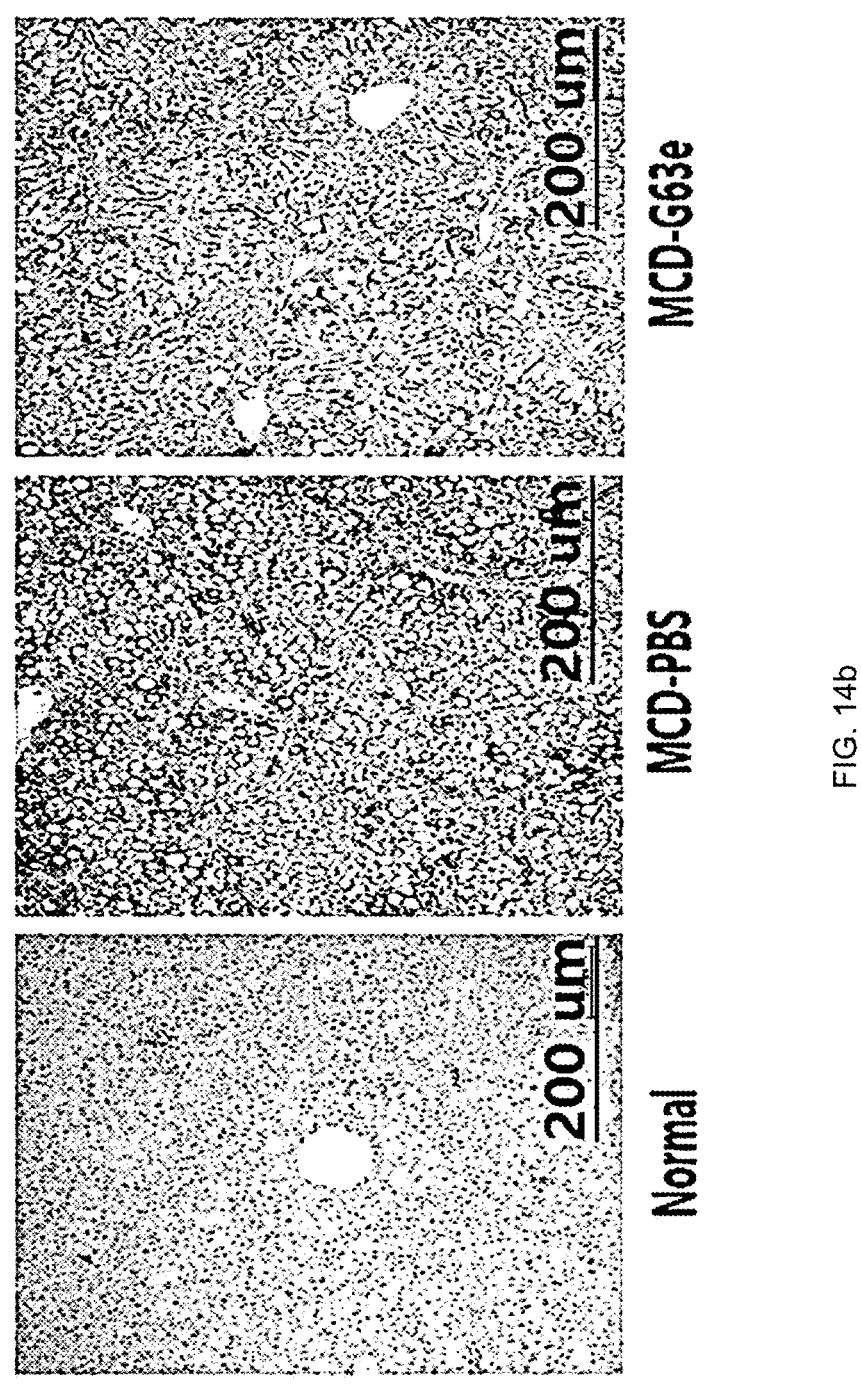
FIG. 14*b* shows microphotographic images of the non-treated normal group (Normal), the PBS-treated control (MCD-PBS), and the BxC-G63e-treated group (MCD-G63e) of hepatocytes from steatosis-induced mice after immunohistochemical staining.

As shown in FIGS. 14a and 14b, the groups which had been treated with BxC-G63e or BxC-V37e after induction of steatosis with MCD diet were observed to remarkably decrease in the expression level of TNF-α protein, compared to the PBS-treated control. In addition, as shown in FIG. 13a, low inflammation scores were imparted to the groups treated with BxC-V37e. Therefore, the data show that BxC-G63e or BxC-V37e has excellent inhibitory activity against inflammation.

Experimental Example 7: Assay for Non-Alcoholic Steatohepatitis of BxC-V37e and BxC-G63e in TAA Mouse Model The following experiments were conducted with the exosomes isolated in Examples 2-1 (BxC-V37e) and 2-2 (BxC-G63e).
7-1. Fibrosis Induction in TAA Mouse
TAA Diet Mouse Raising Condition C57BL/6 male mice were raised in the environment which was set for temperature 23±3° C., relative humidity 55±15%, ventilation 10-20 times/hr, lightening 12 hours (light on a.m. 8-light off p.m. 8), and illumination intensity 150-300 Lux. The environment was monitored regularly.
TAA Drug Administration To the C57BL/6 male mice 6 weeks old, TAA was administered at a dose of 200 mg/kg once a day and three times a week for 12 weeks.
Preparation and Administration of Test Substance BxC-G63e and BxC-V37e were diluted in PBS to prepare respective test substances. The test substance was subcutaneously injected at a dose of 400 μg/head once a day and three times a week for 4 weeks. At the same time, TAA was injected at a dose of 200 mg/kg once a day and twice a week for 4 weeks. For injection of the substance, the injection site was sterilized with 70% alcohol. The skin of the right thigh in the mouse was pulled with the thumb and index finger to create a space between the skin and the muscle. An insulin syringe was poked into the subcutaneous space created with the thumb and index finger from the front of the animal and administered as it was.

7-2. Assay for Therapeutic Activity for Non-Alcoholic Steatohepatitis

The liver was excised from the C57BL/6 male mice injected with the test substance, photographed, and weighed. The right lobe was fixed in 10% neutral buffered formalin while the left lobe was quenched with liquid nitrogen before use in the following experiments.
① Inhibitory Effect on Fibrosis
Histopathological Examination After general tissue processes including trimming, dehydration, paraffin embedding, and sectioning, the fixed liver tissue was prepared into specimens for histopathological examination. The specimens were stained with hematoxylin & eosin (H&E) and picrosirius red and examined for histopathological change under an optical microscope (Olympus BX53, Japan).

Figure 15A:
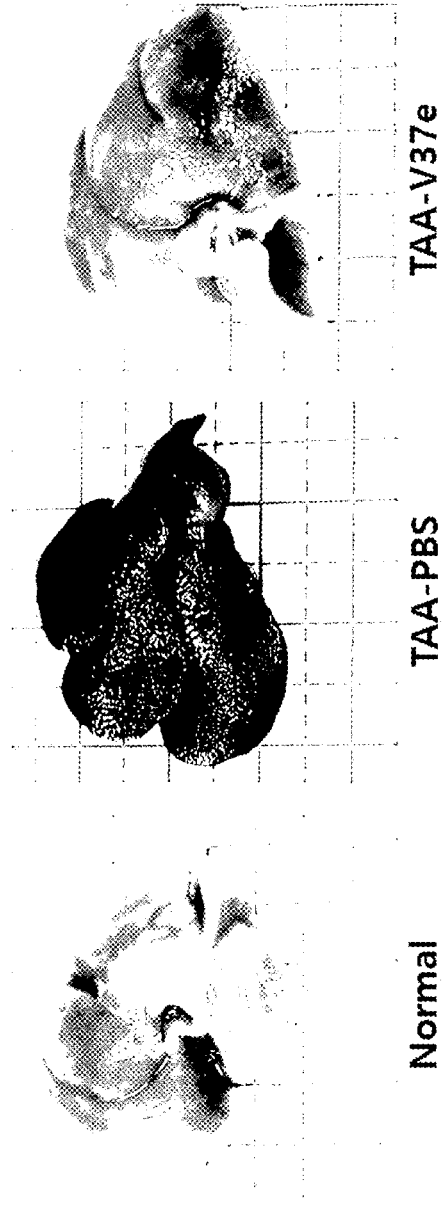
FIG. 15*a* shows photographic images of the non-treated normal group (Normal), the PBS-treated control (TAA-PBS), and the BxC-V37e-treated group (TAA-V37e) of liver tissues from fibrosis-induced mice.
Figure 15B:
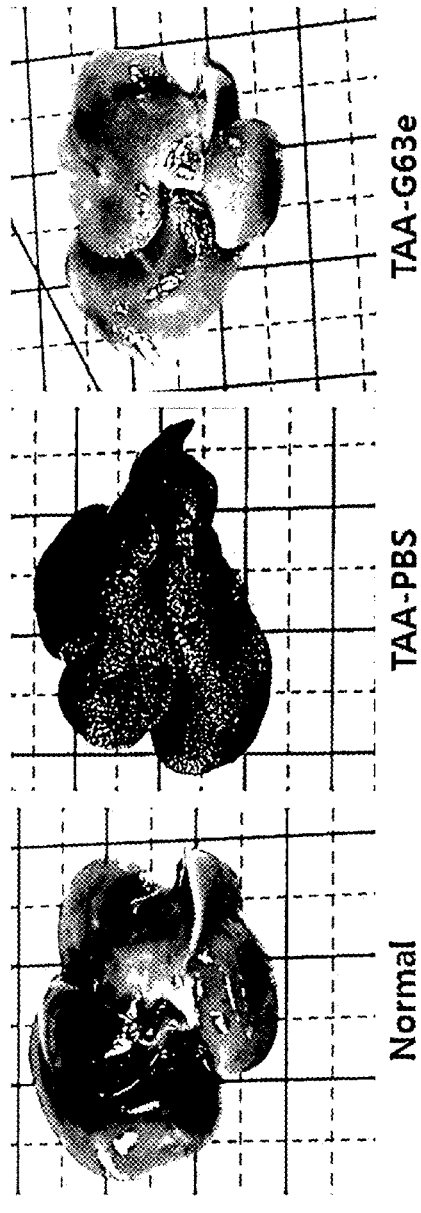
FIG. 15*b* shows photographic images of the non-treated normal group (Normal), the PBS-treated control (TAA-PBS), and the BxC-G63e-treated group (TAA-G63e) of liver tissues from fibrosis-induced mice.

As shown in FIGS. 15a and 15b, the liver tissue of the TAA-PBS group was not smooth, compared to that of the non-treated, normal group. Treatment with BxC-G63e or BxC-V37e was observed to significantly recover the liver tissue.

Figure 16A:
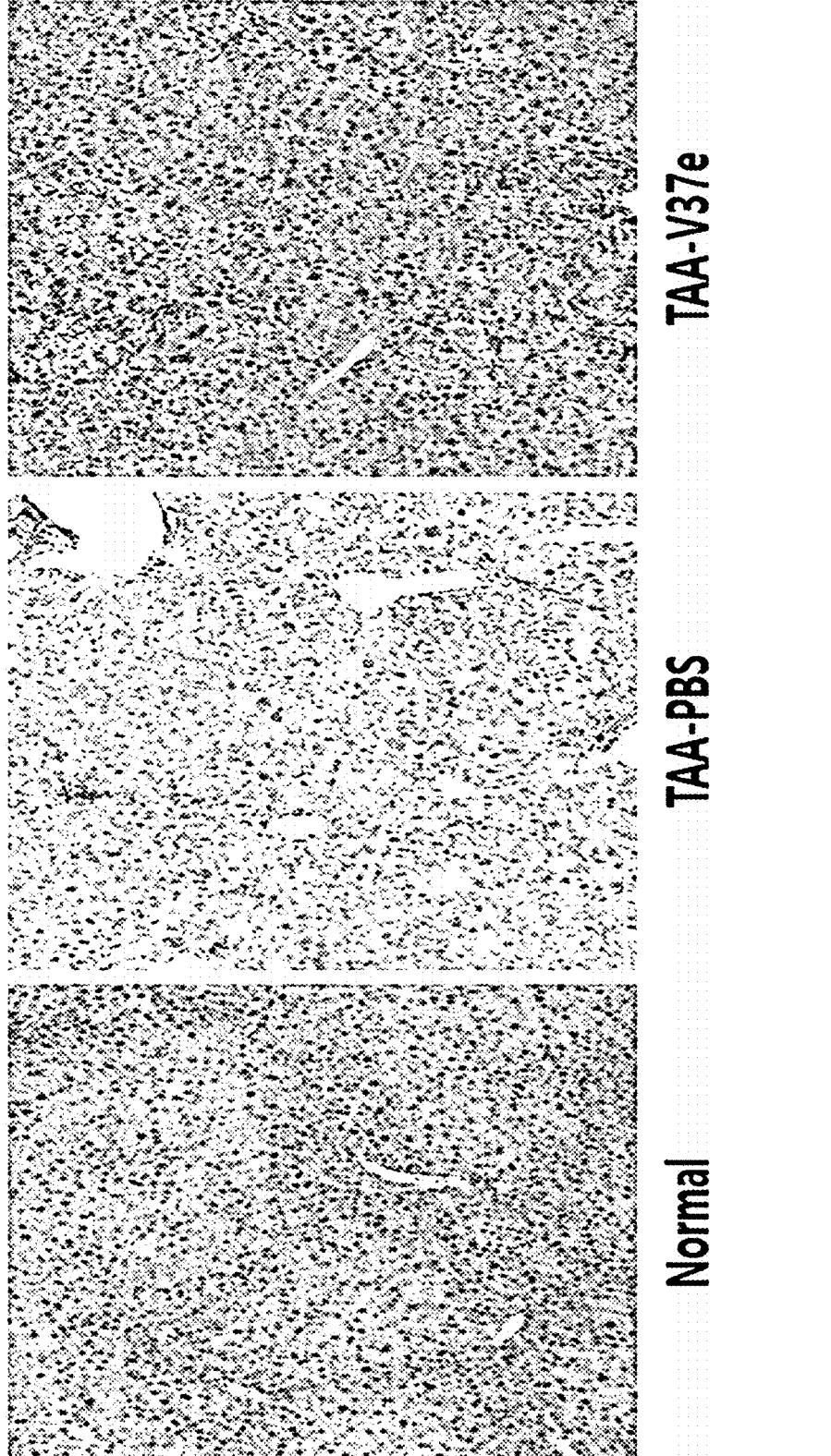
FIG. 16*a* shows microphotographic images of the non-treated normal group (Normal), the PBS-treated control (TAA-PBS), and the BxC-V37e-treated group (TAA-V37e) of hepatocytes from fibrosis-induced mice after hematoxylin & eosin (H&E) staining.
Figure 16B:
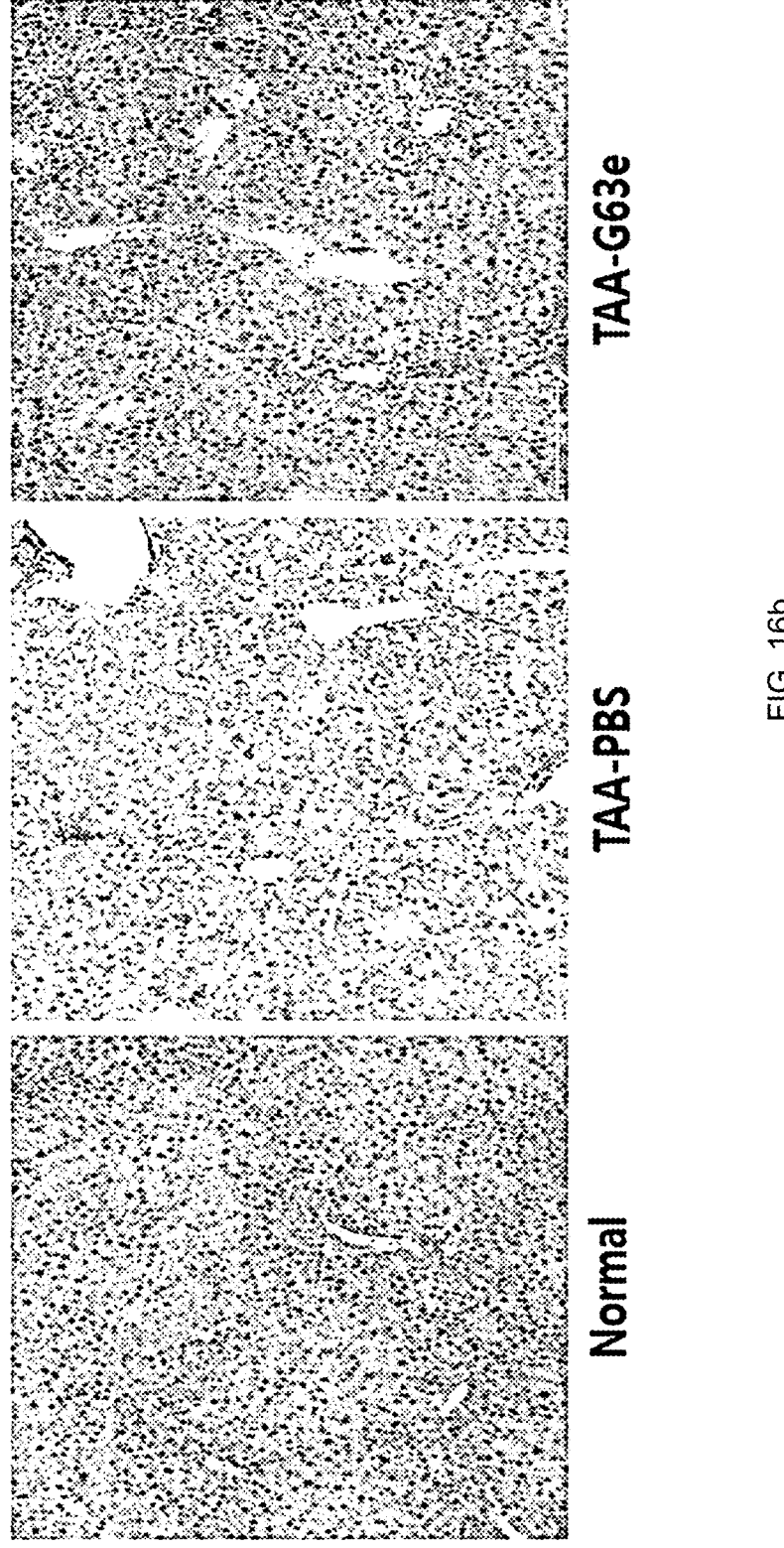
FIG. 16*b* shows microphotographic images of the non-treated normal group (Normal), the PBS-treated control (TAA-PBS), and the BxC-G63e-treated group (TAA-G63e) of hepatocytes from fibrosis-induced mice after hematoxylin & eosin (H&E) staining.

In addition, as can be seen in FIGS. 16a and 16b, H&E staining results showed the liver tissue damaged by TAA was remarkably recuperated by BxC-G63e or BxC-V37e.

Figure 17A:
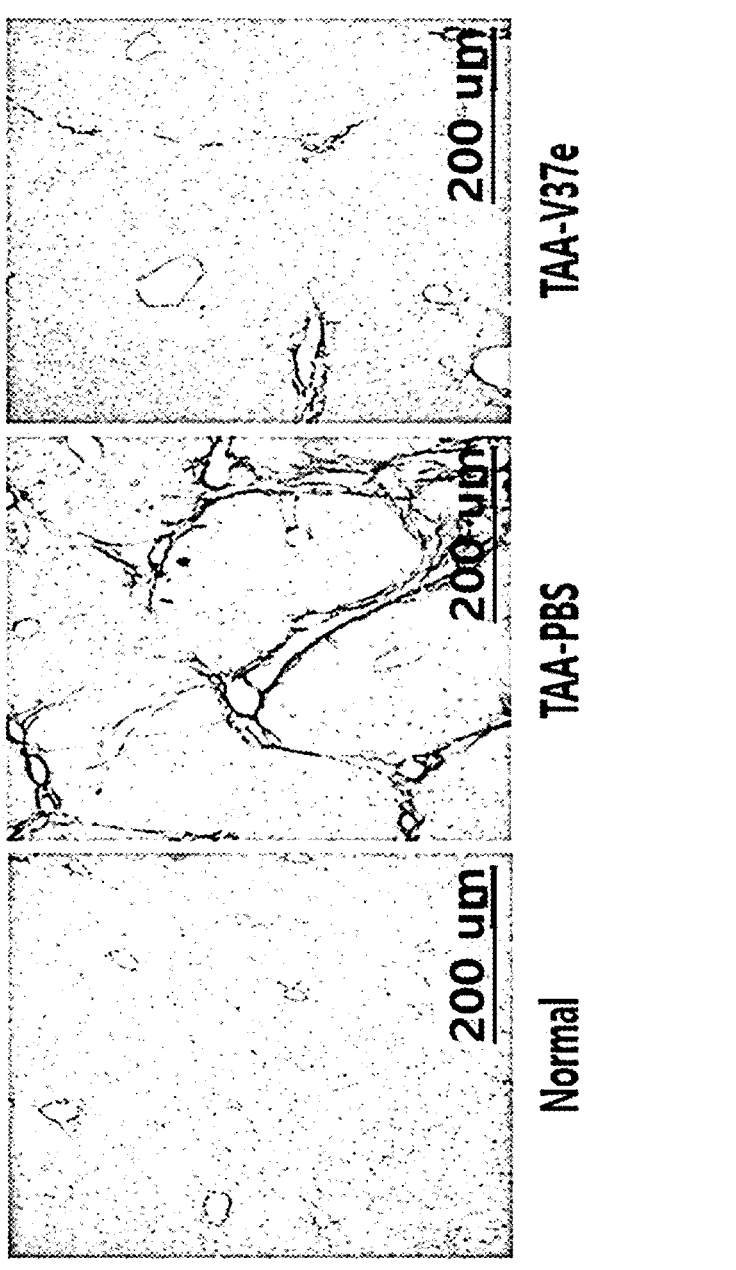
FIG. 17*a* shows microphotographic images of the non-treated normal group (Normal), the PBS-treated control (TAA-PBS), and the BxC-V37e-treated group (TAA-V37e) of hepatocytes from fibrosis-induced mice after picrosirius red staining.
Figure 17B:
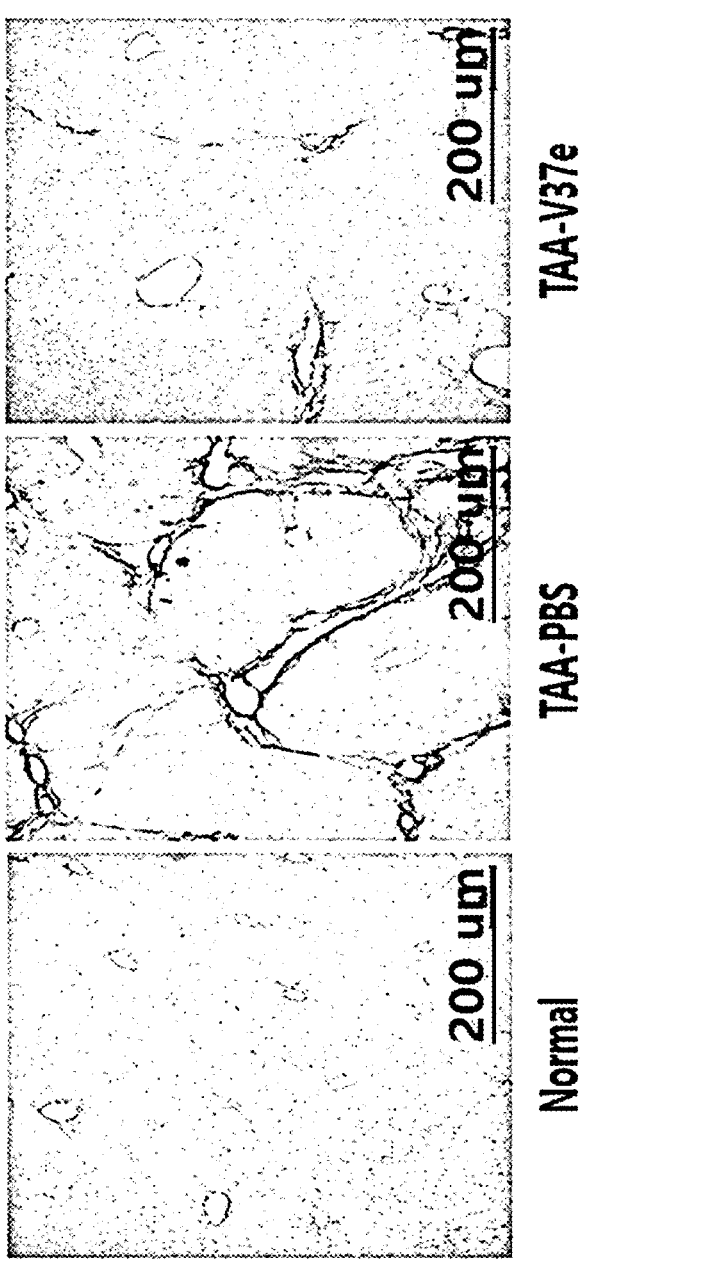
FIG. 17*b* shows microphotographic images of the non-treated normal group (Normal), the PBS-treated control (TAA-PBS), and the BxC-G63e-treated group (TAA-G63e) of hepatocytes from fibrosis-induced mice after picrosirius red staining.

The picrosirius red staining data of FIGS. 17a and 17b show that the amounts of collagen accumulated by TAA in the liver tissues were greatly reduced by BxC-G63e or BxC-V37e.

Collectively, the data demonstrate that BxC-G63e or BxC-V37e has excellent inhibitory activity against fibrosis.

Conclusion

As described hitherto, BxC-e, BxC-V37e, and BxC-G63e according to the present disclosure is understood to inhibit lipogenesis, inflammation, and ER stress in steatosis-induced hepatocytes, thus finding highly advantageous applications in preventing or treating non-alcoholic steatohepatitis.

INDUSTRIAL APPLICABILITY

The present disclosure relates to a composition for prevention or treatment of non-alcoholic steatohepatitis, the composition comprising, as an active ingredient, exosomes isolated from induced pluripotent stem cell-derived mesenchymal stem cells which have been or have not been treated with a pretreatment material.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A method for treating non-alcoholic steatohepatitis, comprising step of:

administering, to a subject, a composition comprising exosomes isolated from induced pluripotent stem cell-derived mesenchymal stem cells (MSC) treated with a pretreatment material selected from the group consisting of 1-(6-benzothiazolysulfonyl)-5-chloro-1H-indole-2-butanoic acid and exendin-4;

wherein the induced pluripotent stem cell-derived mesenchymal stem cells are derived from a progenitor of induced pluripotent stem cell-derived mesenchymal stem cells which does not express SSEA-4 (stage-specific embryonic antigen 4) protein, wherein the exosomes do not contain the pretreatment material.

2. The method of claim 1, wherein the induced pluripotent stem cells are induced pluripotent stem cells of human origin.

* * * * *

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: FABP4-F

<400> SEQUENCE: 1
gcatggccaa acctaacatg                                     20

<210> SEQ ID NO 2
<211> LENGTH: 20
<212> TYPE: DNA
<213> ORGANISM: Artificial Sequence
<220> FEATURE:
<223> OTHER INFORMATION: FABP4-R

<400> SEQUENCE: 2
cctggcccag tatgaaggaa                                     20

<210> SEQ ID NO 3
<211> LENGTH: 24
<212> TYPE: DNA
<213> ORGANISM: Artificial Sequence
<220> FEATURE:
<223> OTHER INFORMATION: TNFa-F

<400> SEQUENCE: 3
gagctgaaca ataggctgtt ccca                                24

<210> SEQ ID NO 4
<211> LENGTH: 24
<212> TYPE: DNA
<213> ORGANISM: Artificial Sequence
<220> FEATURE:
<223> OTHER INFORMATION: TNFa-R

<400> SEQUENCE: 4
agaggctcag caatgagtga cagt                                24

<210> SEQ ID NO 5
<211> LENGTH: 20
<212> TYPE: DNA
<213> ORGANISM: Artificial Sequence
<220> FEATURE:
<223> OTHER INFORMATION: MCP1-F

<400> SEQUENCE: 5
tctgtgcctg ctgctcatag                                     20

<210> SEQ ID NO 6
<211> LENGTH: 20
<212> TYPE: DNA
<213> ORGANISM: Artificial Sequence
<220> FEATURE:
<223> OTHER INFORMATION: MCP1-R

<400> SEQUENCE: 6
gggcattgat tgcatctggc                                     20

<210> SEQ ID NO 7
<211> LENGTH: 24
<212> TYPE: DNA
<213> ORGANISM: Artificial Sequence

```
<220> FEATURE:
<223> OTHER INFORMATION: CHOP-F

<400> SEQUENCE: 7
agggagaacc aggaaacgga aaca                                          24

<210> SEQ ID NO 8
<211> LENGTH: 24
<212> TYPE: DNA
<213> ORGANISM: Artificial Sequence
<220> FEATURE:
<223> OTHER INFORMATION: CHOP-R

<400> SEQUENCE: 8
tcctgcttga gccgttcatt ctct                                          24

<210> SEQ ID NO 9
<211> LENGTH: 20
<212> TYPE: DNA
<213> ORGANISM: Artificial Sequence
<220> FEATURE:
<223> OTHER INFORMATION: ACC1-F

<400> SEQUENCE: 9
gctccttgtc acctgcttct                                               20

<210> SEQ ID NO 10
<211> LENGTH: 20
<212> TYPE: DNA
<213> ORGANISM: Artificial Sequence
<220> FEATURE:
<223> OTHER INFORMATION: ACC1-R

<400> SEQUENCE: 10
caaggccaag ccatcctgta                                               20

<210> SEQ ID NO 11
<211> LENGTH: 20
<212> TYPE: DNA
<213> ORGANISM: Artificial Sequence
<220> FEATURE:
<223> OTHER INFORMATION: SREBP1-F

<400> SEQUENCE: 11
ggaggggtag gggccaacgc                                               20

<210> SEQ ID NO 12
<211> LENGTH: 20
<212> TYPE: DNA
<213> ORGANISM: Artificial Sequence
<220> FEATURE:
<223> OTHER INFORMATION: SREBP1-R

<400> SEQUENCE: 12
catgtcttcg aaagtgcaat                                               20

<210> SEQ ID NO 13
<211> LENGTH: 20
<212> TYPE: DNA
<213> ORGANISM: Artificial Sequence
<220> FEATURE:
<223> OTHER INFORMATION: IL10-F

<400> SEQUENCE: 13
tgaaaacaag agcaaggccg                                               20
```

-continued

```
<210> SEQ ID NO 14
<211> LENGTH: 20
<212> TYPE: DNA
<213> ORGANISM: Artificial Sequence
<220> FEATURE:
<223> OTHER INFORMATION: IL10-R

<400> SEQUENCE: 14
gccaccctga tgtctcagtt                                                                     20
```